(12) United States Patent
Zeng et al.

(10) Patent No.: US 11,931,423 B2
(45) Date of Patent: Mar. 19, 2024

(54) GLUCOSE OXIDASE-NANOPARTICLE BIOCONJUGATES FOR CANCER TREATMENT

(71) Applicant: UNIVERSITY OF PITTSBURGH—OF THE COMMONWEALTH SYSTEM OF HIGHER EDUCATION, Pittsburgh, PA (US)

(72) Inventors: Dexing Zeng, Pittsburgh, PA (US); Di Gao, Sewickley, PA (US); Jiamin Wu, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 373 days.

(21) Appl. No.: 16/691,030

(22) Filed: Nov. 21, 2019

(65) Prior Publication Data
US 2020/0085966 A1 Mar. 19, 2020

Related U.S. Application Data

(63) Continuation of application No. PCT/US2018/034554, filed on May 25, 2018.

(60) Provisional application No. 62/511,717, filed on May 26, 2017.

(51) Int. Cl.
| | |
|---|---|
| *A61K 47/68* | (2017.01) |
| *A61B 5/0515* | (2021.01) |
| *A61B 5/055* | (2006.01) |
| *A61K 47/69* | (2017.01) |
| *A61P 35/00* | (2006.01) |
| *C07K 16/28* | (2006.01) |
| *C07K 16/32* | (2006.01) |

(52) U.S. Cl.
CPC ........ *A61K 47/6815* (2017.08); *A61B 5/0515* (2013.01); *A61B 5/055* (2013.01); *A61K 47/6811* (2017.08); *A61K 47/6851* (2017.08); *A61K 47/6923* (2017.08); *A61P 35/00* (2018.01); *C07K 16/2827* (2013.01); *C07K 16/2842* (2013.01); *C07K 16/2863* (2013.01); *C07K 16/2866* (2013.01); *C07K 16/32* (2013.01)

(58) Field of Classification Search
CPC .. A61K 47/6923; A61K 47/68; A61K 47/681; C07K 16/28; C07K 16/32
See application file for complete search history.

(56) References Cited

U.S. PATENT DOCUMENTS

| | | | | |
|---|---|---|---|---|
| 2008/0076139 A1* | 3/2008 | Singh | ............... | G01N 33/57496 435/7.23 |
| 2011/0268654 A1* | 11/2011 | Hilderbrand | ....... | A61K 51/0474 424/9.4 |
| 2014/0178901 A1* | 6/2014 | Weissleder | ........... | G01N 33/587 435/7.23 |
| 2014/0228290 A1 | 8/2014 | Spitz et al. | | |
| 2014/0241996 A1 | 8/2014 | Medarova et al. | | |

FOREIGN PATENT DOCUMENTS

| | | | | |
|---|---|---|---|---|
| WO | WO2017023855 | * | 2/2017 | ............. C12P 19/36 |
| WO | WO2018094005 | * | 5/2018 | ............. A61K 51/04 |

OTHER PUBLICATIONS

Abbasi et al., Improvement of the stability and activity of immobilized glucose oxidase on modified iron oxide magnetic nanoparticles. Applied surface Science, 364, 752-757, 2016. (Year: 2016).*
Divakaran et al., "D-Aminoacid Oxidase-$Fe_2O_3$ Nanoparticle Complex Mediated Antitumor Activity in Swiss Albino Mice," Journal of Cancer Therapy, 2:666-674 (2011).
Huo et al., "Tumor-selective catalytic nanomedicine by nanocatalyst delivery," Nature Communications, 8:357 (2017).
International Search Report and Written Opinion dated Aug. 21, 2018 in International Application No. PCT/US2018/034554.
Misra et al., "CXCR4-Targeted Nanocarriers for Triple Negative Breast Cancers," Biomacromolecules 16(8):2412-2417 (2015).
Rossi et al., "Glucose oxidase-magnetite nanoparticle bioconjugate for glucose sensing," Anal Bioanal Chem. 380(4):606-613 (2004).
Tseng et al., "Cetuximab-conjugated iron oxide nanoparticles for cancer imaging and therapy," Int J Nanomedicine 10:3663-3685 (2015).
Wikipedia, "Iron oxide nanoparticle" Version: Mar. 26, 2017 (Mar. 26, 2017). Retrieved: Aug. 1, 2018 (Aug. 1, 2018) (https://en.wikipedia.org/w/index.php?title=Iron_oxide_nanoparticle&oldid=772231196) p. 1, para 1.

* cited by examiner

*Primary Examiner* — Elly-Gerald Stoica
(74) *Attorney, Agent, or Firm* — Baker Botts L.L.P.

(57) ABSTRACT

Bioconjugates and methods of making bioconjugates are provided, wherein the bioconjugates comprise glucose oxidase and nanoparticles that can kill tumor cells. For example, glucose oxidase-iron oxide bioconjugates can produce reactive oxygen species from blood glucose, causing cell death. The use of superparamagnetic iron oxide nanoparticles can provide magnetic resonance imaging guidance to facilitate imaging-guided drug delivery and combine diagnostics with therapy.

7 Claims, 14 Drawing Sheets

GLUCOSE OXIDASE-NANOPARTICLE BIOCONJUGATES FOR CANCER TREATMENT

PRIORITY CLAIM

This patent application is a continuation of, and claims priority to, International Patent Application No. PCT/US2018/034554, filed on May 25, 2018, which claims priority to U.S. Provisional Patent Application Ser. No. 62/511,717, filed May 26, 2017, the content of which are hereby incorporated by reference in their entireties, and to which priority is claimed.

1. INTRODUCTION

The presently disclosed subject matter relates to bioconjugates of glucose oxidase and a nanoparticle and the preparation of such bioconjugates. The presently disclosed bioconjugates can be used for the targeted destruction of tumor cells for the treatment of cancer.

2. BACKGROUND OF THE INVENTION

Cancer is the general name for a group of more than 100 diseases and can be defined as an uncontrolled proliferation of cells that usually invade adjacent local tissues and often spread, via lymphatic and blood vessels, to distant parts of the body giving rise to metastases including dispersed (such as lymphomas and leukemias) and solid tumors (such as in the lung and brain). Despite the progress and promise of current cancer therapies, the survival rate for some of major cancers remains very low. For example, the 5-year survival rate is only 15% for lung cancer patients, and if the patients are diagnosed with advanced stage (metastatic) lung cancer, the 5-year survival rate is less than 1%. As a result, there has been steadily growing interest in and demand for development of more effective therapies.

Reactive oxygen species (ROS) are broadly defined as oxygen-containing, reactive chemical species, including singlet oxygen ($O_2$; also referred to as $^1O_2$), superoxide anions ($.O_2^-$), and hydroxyl radicals (.OH). ROS can be generated inside of cells through multiple mechanisms, and are essential for biological functions. They regulate many signal transduction pathways by directly reacting with the proteins, transcription factors, and/or genes to modulate their functions. A mild increase in the level of ROS can result in transient cellular alteration, whereas a severe increase in the level of ROS in cells can cause irreversible oxidative damage, leading to cell death through apoptosis and necrosis. Under certain situations, ROS can also induce cell death through autophagy, which is a self-catabolic process and involves the sequestration and degradation of cytoplasmic contents.

ROS-induced anti-neoplastic therapies have been clinically used as a noninvasive approach for cancer treatment. Examples include radiotherapy, recognized as one of the most common cancer treatments, and photodynamic therapy (PDT). However, both radiotherapy and PDT have significant limitations and side effects. Radiotherapy relies on ROS toxicity to promote ROS-mediated cancer cell death and mitotic failure. During radiotherapy, the level of ROS is dramatically increased by using either X-rays, γ-rays, or heavy particle radiation such as protons and neutrons, which, in addition to a therapeutic toxic effect against cancer cells, can also cause unwanted collateral damage to healthy tissue. Another example of ROS-induced therapy is PDT therapy, which uses ROS generated by irradiating a nontoxic photosensitizer with an appropriate wavelength of light in the presence of molecular oxygen to destroy tumor cells. Although the principle of photodynamic therapy is simple, in practice, the dosimetry of the drug and the light, as well as the interval between drug and light administration is critical and challenging to control. In addition, PDT is limited by the penetration depth of light exciting the photosensitizers.

Therefore, there remains a need in the art for improved noninvasive therapies for cancer treatment that induce cell death by increasing the level of ROS.

3. SUMMARY OF THE INVENTION

The presently disclosed subject matter relates to bioconjugates that comprise glucose oxidase (GOx) and a nanoparticle, and methods of making and using them. For example, a nanoparticle conjugated to GOx can comprise iron oxide. In certain embodiments, glucose oxidase-iron oxide bioconjugates can produce reactive oxygen species (ROS) from blood glucose that can be utilized therapeutically to cause cell death. The bioconjugates can further include targeting probes, such as an antibody or a fragment thereof, a small molecule, a protein or a peptide, to facilitate specific binding of the bioconjugates to their cell target, e.g., tumor cells. The use of superparamagnetic iron oxide nanoparticles (SPION) can provide magnetic resonance imaging (MRI) guidance to facilitate imaging-guided drug delivery.

Thus, in certain aspects, the presently disclosed subject matter provides bioconjugates for causing cell death in tumor cells including an iron oxide nanoparticle and glucose oxidase conjugated to the iron oxide nanoparticle. In particular non-limiting embodiments, the iron oxide nanoparticles can be superparamagnetic iron oxide nanoparticles (SPION).

As embodied herein, the bioconjugate can further include a targeting probe conjugated to the glucose oxidase for specifically binding to the tumor cells. Alternatively or additionally, a targeting probe can be conjugated to the iron oxide nanoparticle(s) for specifically binding to the tumor cells. The presently disclosed subject matter further relates to pharmaceutical compositions including an effective amount of such bioconjugates, as well as therapeutic methods of using them.

In certain non-limiting embodiments, the targeting probe can be a monoclonal antibody, an antibody fragment, a protein, a peptide, and/or a small molecule. For example, in certain embodiments, the targeting probe is a monoclonal antibody selected from UMB2 (ab124824), etaracizumab, E398P (ab32528), cetuximab, bevacizumab, trastuzumab, mAb 8G7, 1116NS19-9, CP-870,893, atezolizumab, and ab92574, etc. In particular embodiments, the monoclonal antibody is cetuximab. In certain embodiments, the targeting probe is a peptide selected from LLP2A, AE105, BBN(7-14), Tyr(3)-octreotate, DAPTA, T140, CPCR4-2, RGD, and PTP, etc. In particular embodiments, the peptide is RGD. In certain embodiments, the targeting probe is a small molecule selected from folic acid, AMD 3100, AMD 3465, and erlotinib, etc. In particular embodiments, the small molecule is AMD 3100. For example, and not limitation, the targeting probe can be specific to an EGFR receptor, an integrin receptor, and/or a chemokine receptor, or a fragment thereof.

The bioconjugate can further include a first spacer disposed between the iron oxide nanoparticle and the glucose oxidase, a second spacer disposed between the iron oxide nanoparticle and the targeting probe and/or a second spacer disposed between the glucose oxidase and the targeting probe. In certain non-limiting embodiments, one or both of the first spacer and the second spacer can include polyethylene glycol.

In certain embodiments, the ratio between the iron oxide nanoparticle and the glucose oxidase is from about 1:100 to about 100:1. In certain embodiments, the ratio between the iron oxide nanoparticle and the glucose oxidase is from about 1:20 to about 20:1.

In certain other aspects, the presently disclosed subject matter provides kits including iron oxide nanoparticles, glucose oxidase, and one or more reagents for conjugating the iron oxide nanoparticles and the glucose oxidase. In certain non-limiting embodiments, the kits can further include targeting probes and one or more reagents for conjugating the targeting probes and the iron oxide nanoparticles and/or the glucose oxidase. In certain non-limiting embodiments, the one or more reagents can be at least one of 1,2-hexadecanediol, oleic acid, oleylamine, aminosilane, tetrazine, TCO-PEG4-NHS, and Tz-PEG-NHS, etc.

For the purpose of example, and not limitation, the iron oxide nanoparticles can be functionalized with a biorthogonal ligation moiety, such as tetrazine. For further example, the targeting probe can be a monoclonal antibody, an antibody fragment, a protein, a peptide, and/or a small molecule. In particular embodiments, the targeting probe can be a monoclonal antibody.

In another aspect, the presently disclosed subject matter further provides methods of causing cell death in tumor cells. Methods of causing cell death can include administering to a subject an effective amount of a bioconjugate including an iron oxide nanoparticle and glucose oxidase conjugated to the iron oxide nanoparticle. In certain non-limiting embodiments, the bioconjugate can also include a targeting probe conjugated to the glucose oxidase and/or the iron oxide nanoparticle for specific binding to the tumor cells. In certain non-limiting embodiments, the targeting probe can be a monoclonal antibody, an antibody fragment, a protein, a peptide, and/or a small molecule. For example, in particular embodiments, the targeting probe can be a monoclonal antibody. Alternatively or additionally, the targeting probe can be specific to an EGFR receptor, an integrin receptor, and/or a chemokine receptor, or a fragment thereof. In certain non-limiting embodiments, the effective amount of the bioconjugate can include from about 0.01 mg Fe/kg to about 50 mg Fe/kg of the subject.

In other embodiments, methods of causing cell death in tumor cells can include administering to a subject an effective amount of a bioconjugate including an iron oxide nanoparticle and glucose oxidase conjugated to the iron oxide nanoparticle and localizing the bioconjugates with respect to the tumor cells using MRI guidance and/or a magnetic field. In certain non-limiting embodiments, the iron oxide nanoparticles can be superparamagnetic and can be manipulated by the MRI guidance and/or magnetic field. In certain non-limiting embodiments, the bioconjugate further includes a targeting probe conjugated to the glucose oxidase and/or the iron oxide nanoparticle for specifically binding to tumor cells. In certain non-limiting embodiments, the effective amount of the bioconjugate includes from about 0.01 mg Fe/kg to about 50 mg Fe/kg of the subject.

In yet another aspect, the presently disclosed subject matter provides methods of making bioconjugates for destroying tumor cells. Methods can include conjugating glucose oxidase with an iron oxide nanoparticle to form the bioconjugate. In certain non-limiting embodiments, the method can further include conjugating a targeting probe with glucose oxidase and/or an iron oxide nanoparticle. In certain non-limiting embodiments, conjugating the glucose oxidase and the iron oxide nanoparticle can include functionalizing the iron oxide nanoparticle with first biorthogonal moiety and modifying the glucose oxidase with a second biorthogonal moiety, wherein the iron oxide nanoparticle and the glucose oxidase are conjugated by biorthogonal ligation between the first biorthogonal ligation moiety and the second biorthogonal ligation moiety. In certain non-limiting embodiments, conjugating the glucose oxidase and the targeting probe can include modifying the targeting probe with a third biorthogonal ligation moiety, wherein the glucose oxidase and the targeting probe are conjugated by biorthogonal ligation between the second biorthogonal ligation moiety and the third biorthogonal ligation moiety. As embodied herein, the first, second, and third biorthogonal ligation moieties can be selected from the group consisting of trans-cyclooctene, tetrazine, cyclooctyne, an alkyne, an azide, an alkene, a tetrazole, photo-DIBO, a cyclopropenone, and combinations thereof. In certain non-limiting embodiments, the first biorthogonal ligation moiety is tetrazine, the second biorthogonal ligation moiety is trans-cyclooctene, and/or the third biorthogonal ligation moiety is tetrazine.

In certain non-limiting embodiments, the targeting probe is a monoclonal antibody, an antibody fragment, a protein, a peptide, and/or a small molecule. In certain non-limiting embodiments, the targeting probe is specific to an EGFR receptor, an integrin receptor, and/or a chemokine receptor, or a fragment thereof.

4. BRIEF DESCRIPTION OF THE FIGURES

Figure 5B:
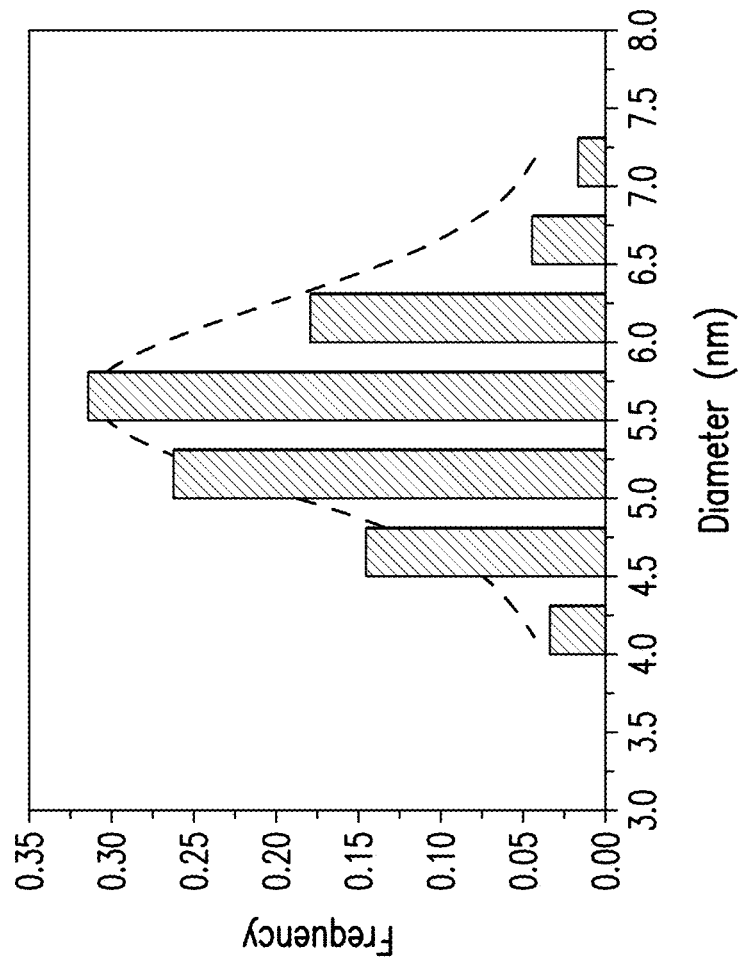
Figure 5A:
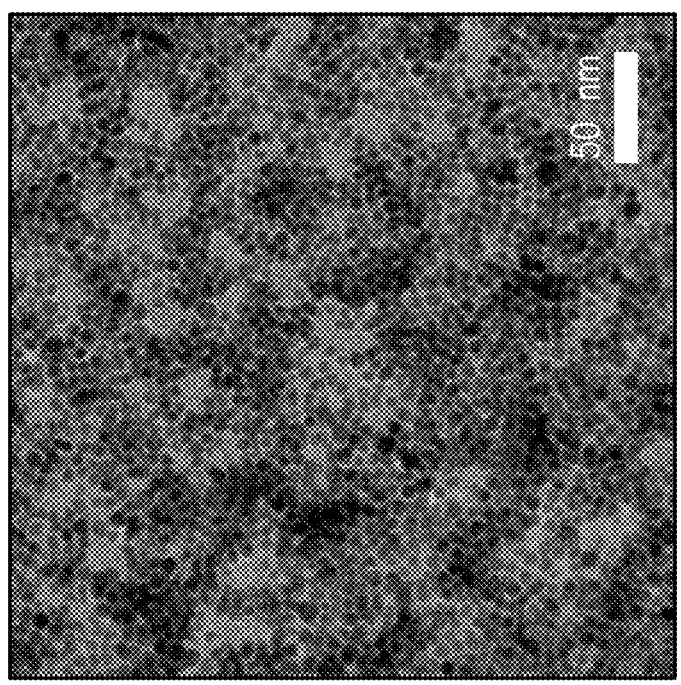

FIG. 5A provides a TEM image of synthesized SPION, as described in Example 1 of the present disclosure.

FIG. 5B provides a size distribution histogram of synthesized SPION, as described in Example 1 of the present disclosure.

Figure 6:
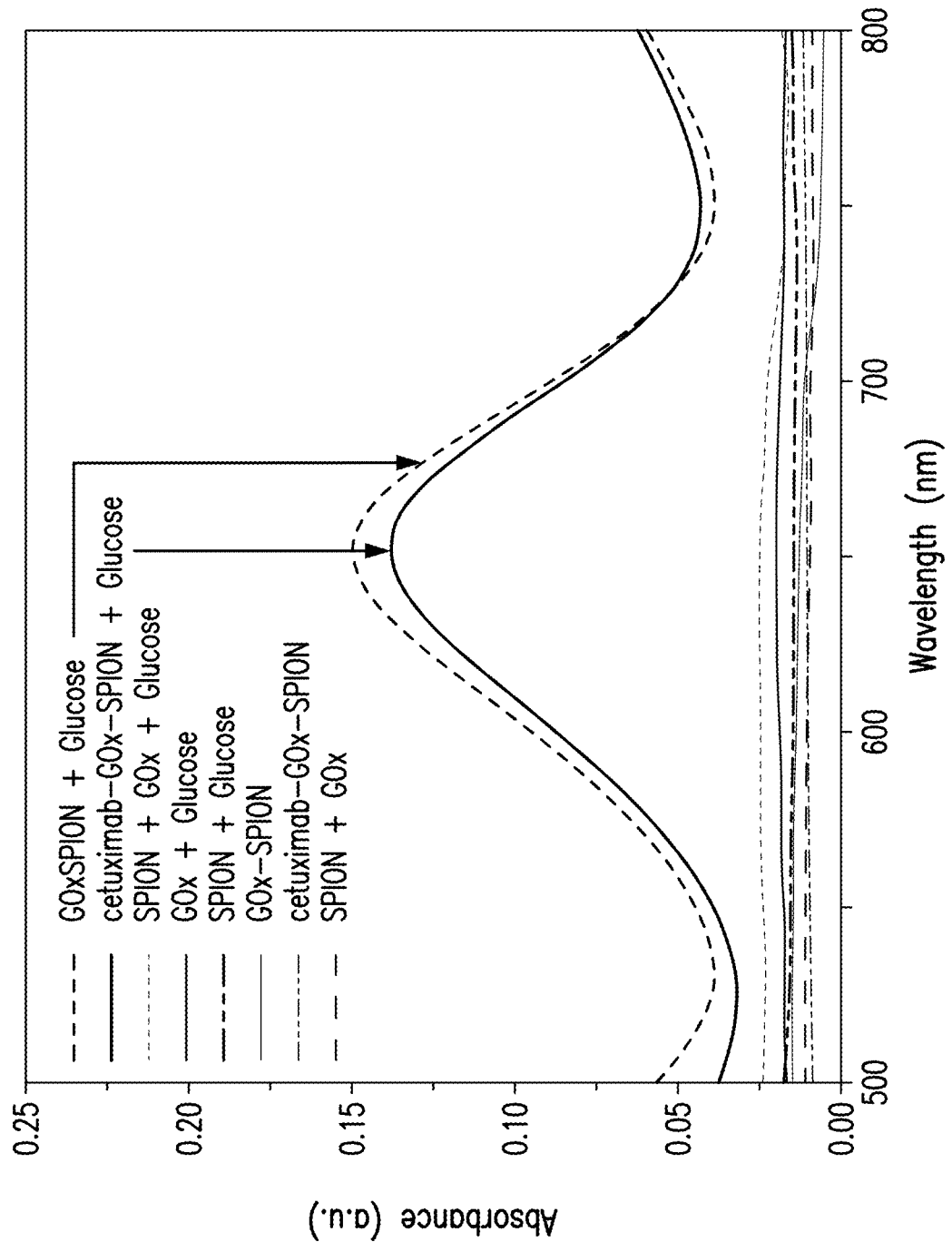

FIG. 6 is a graph depicting the levels of ROS (indicated by the peak height at 650 nm in the UV-vis absorption spectra) produced by GOx and SPION alone, a mixture of GOx and SPION without conjugation, GOx-SPION, and mAb-GOx-SPION, with and without the presence of glucose, as described in Example 2 of the present disclosure.

Figure 7:
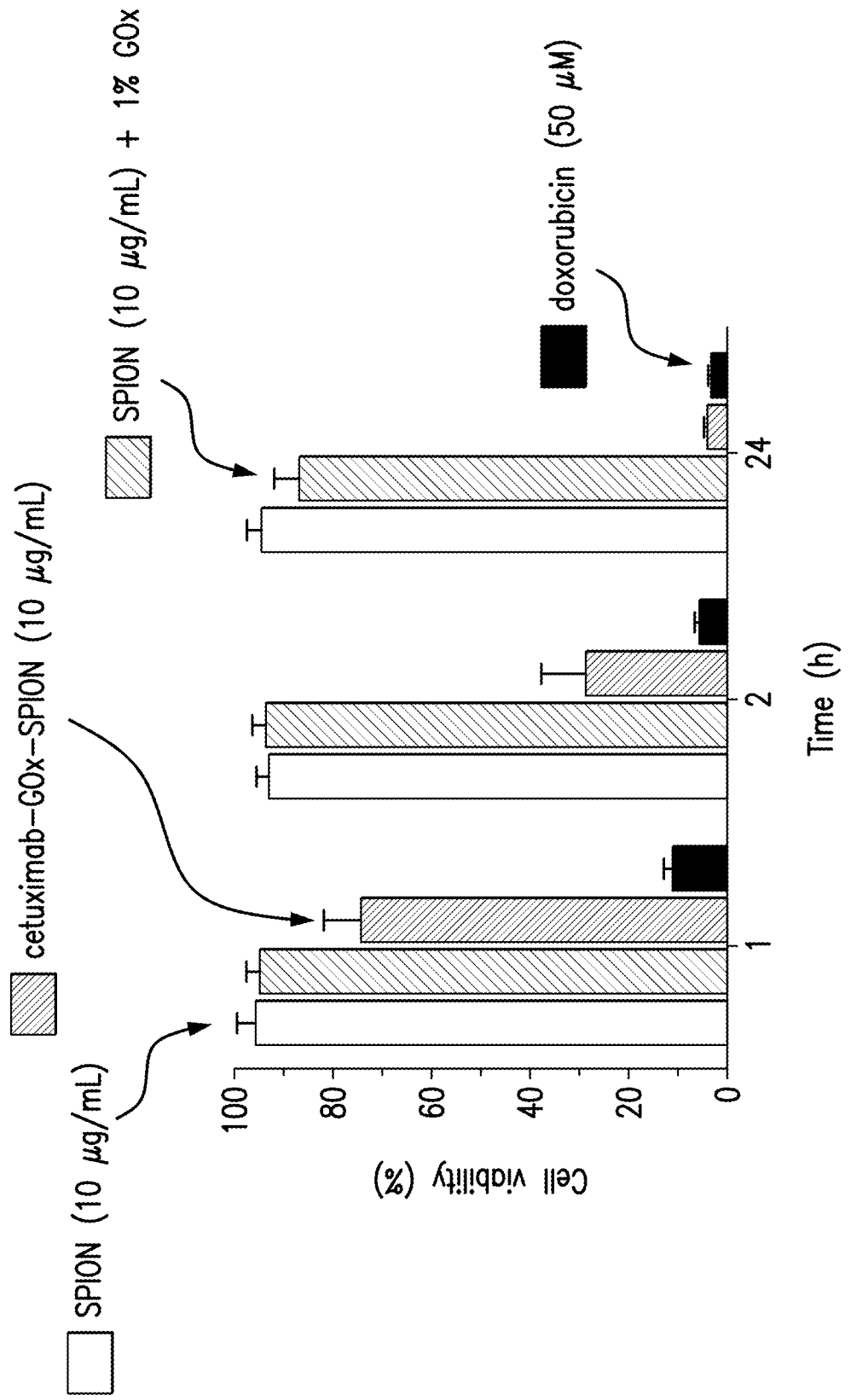

FIG. 7 illustrates the viabilities of A431 cells after treatment with 10 µg/mL SPION, a mixture of unconjugated SPION and GOx, cetuximab-GOx-SPION, and 30 µg/mL doxorubicin for different periods of time (1, 2, and 24 h), as described in Example 3 of the present disclosure.

Figure 8:
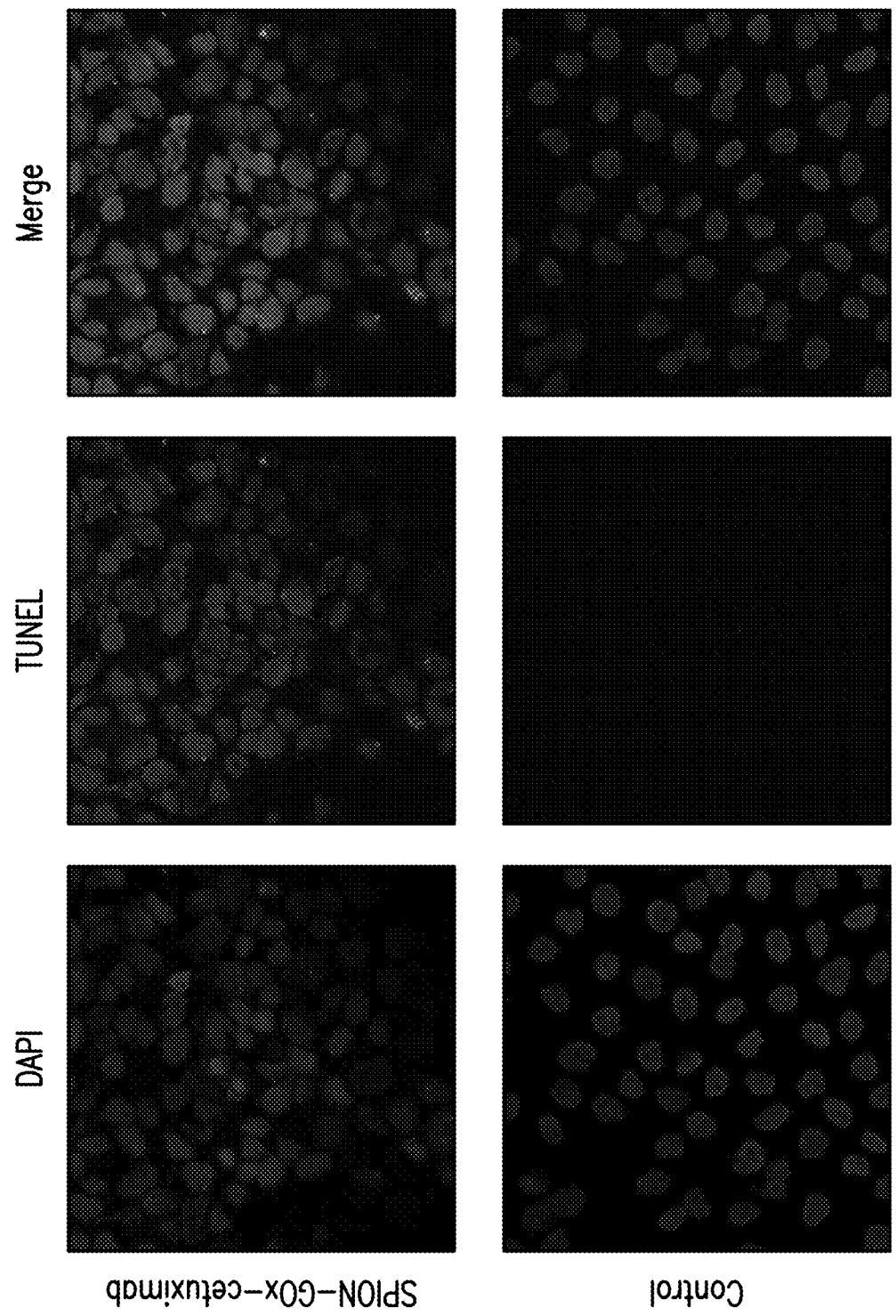

FIG. 8 provides images of an in situ apoptosis detection assay of A431 cells after 18 h treatment with cetuximab- GOx-SPION, as described in Example 3 of the present disclosure. The results of this assay indicate rapid cell death via an apoptosis pathway.

Figure 9:
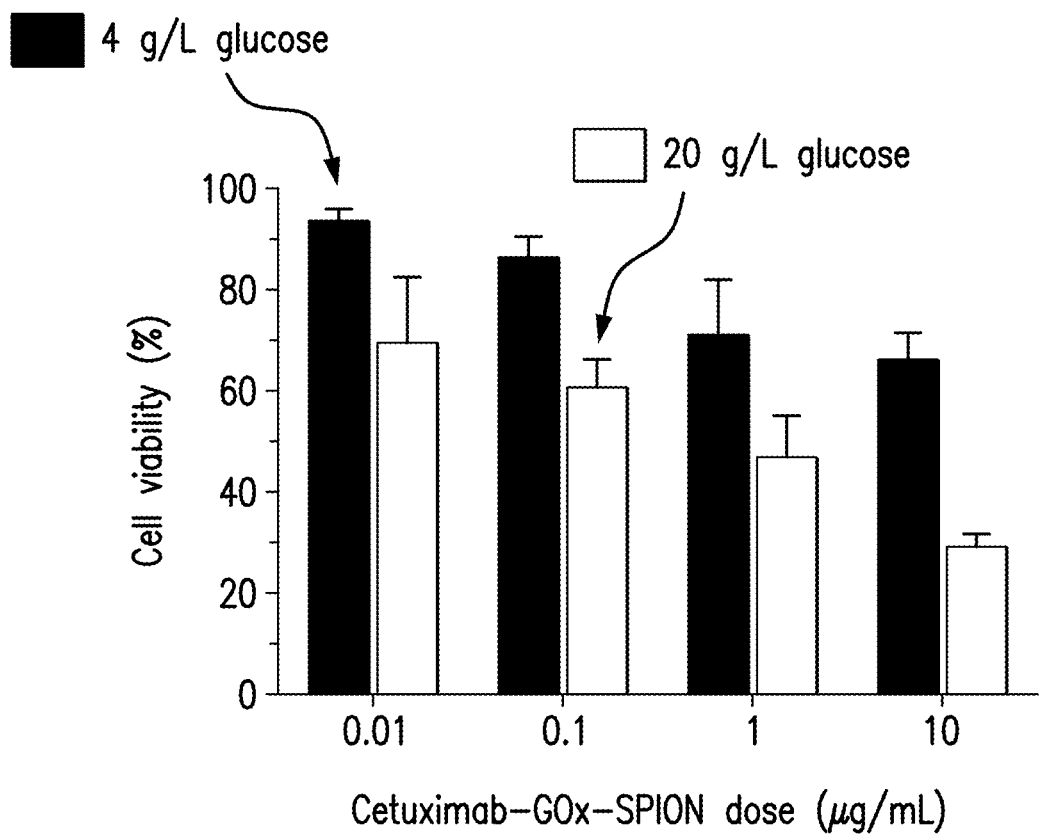

FIG. 9 illustrates the viabilities of A431 cells after 1.5 h treatment with 0.01, 0.1, 1, and 10 µg/mL of cetuximab-GOx-SPION in the presence of 4 g/L and 20 g/L glucose, in accordance with Example 3 of the present disclosure.

Figure 10:
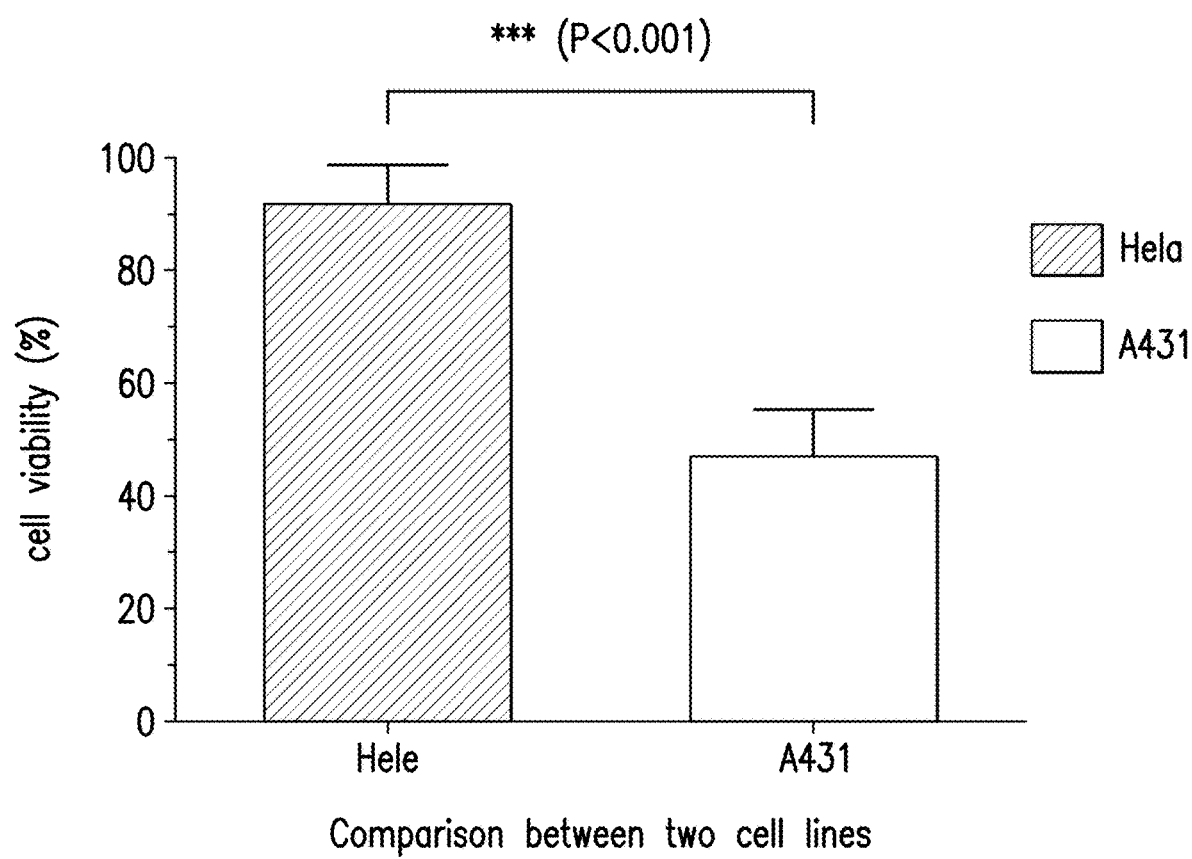

FIG. 10 provides a comparison of the viability of two different cancer cell lines: A431-overexpressed EGFR and HeLa expressing physiological levels of EGFR, as described in Example 4 of the present disclosure.

Figure 11:
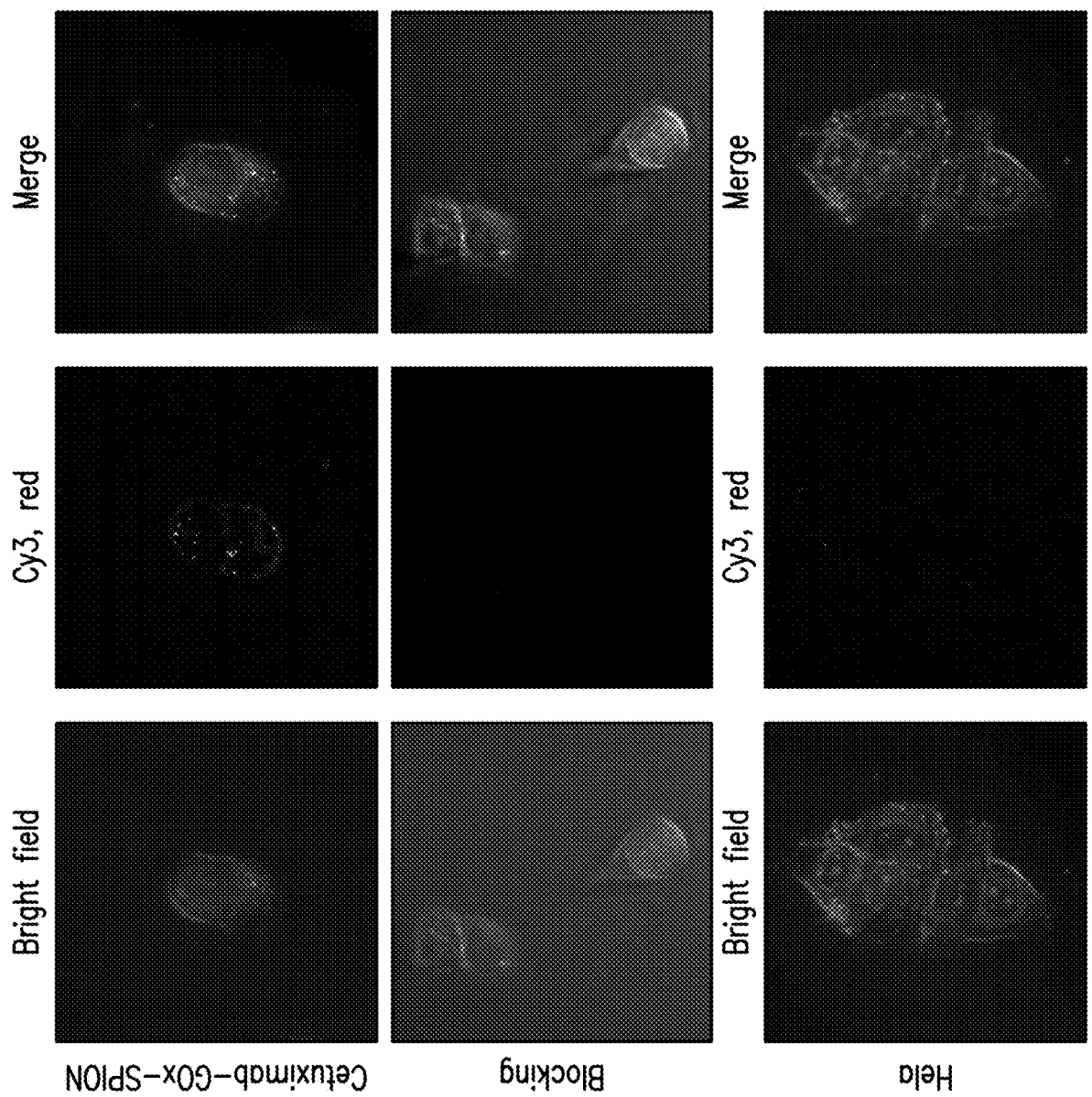

FIG. 11 provides confocal fluorescence microscopy images demonstrating the binding specificity of cetuximab-GOx-SPION to EGFR-overexpressing A431 cells, as described in Example 4 of the present disclosure.

Figure 12A:
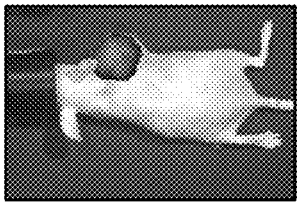
Figure 12B:
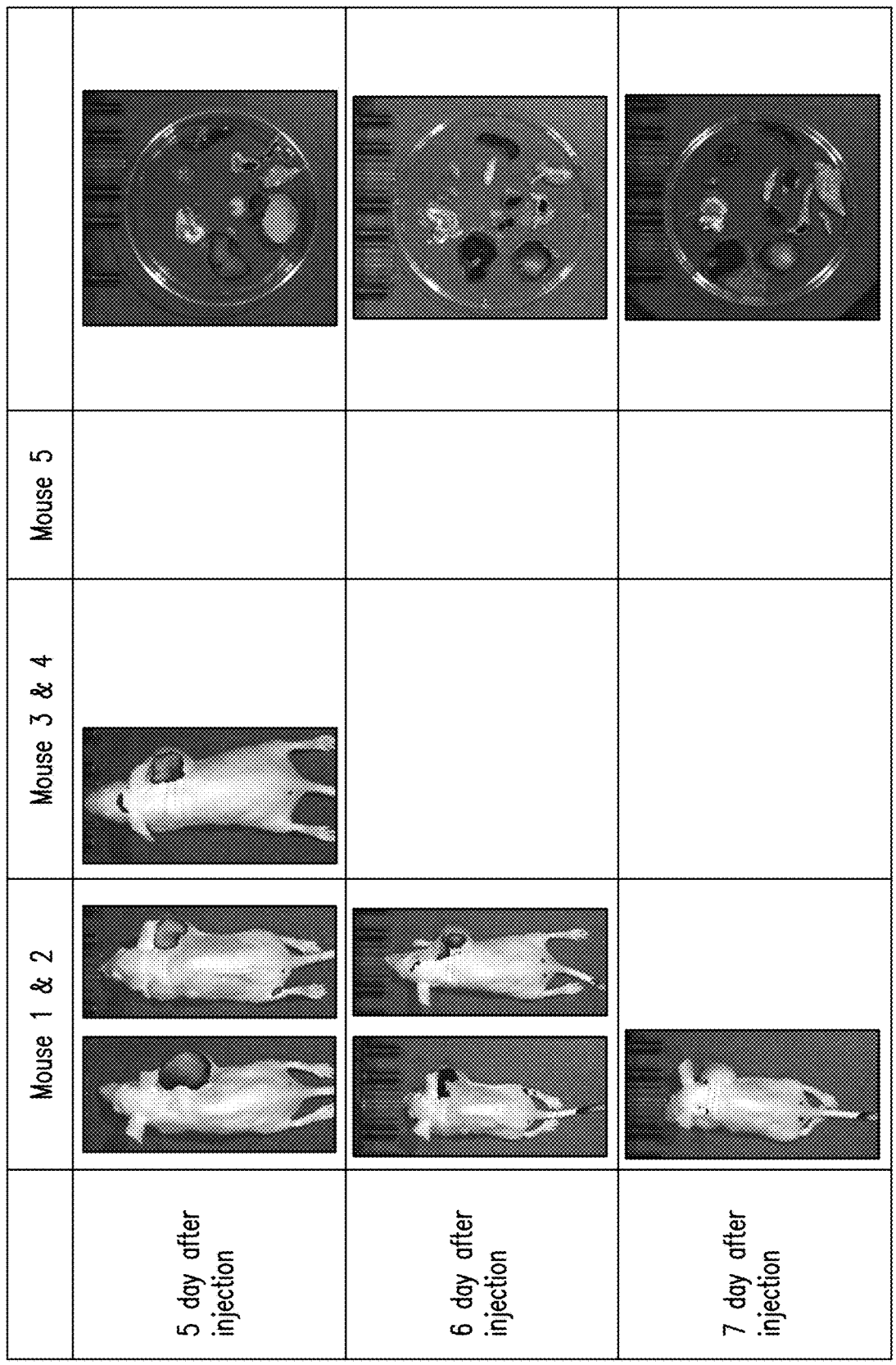

FIGS. 12A-12B provide images of the biodistribution of SPION-GOx-Cy7 bioconjugates in mice that received 4T1 breast cancer xenografts, as described in Example 5 of the present disclosure. FIG. 12A shows the biodistribution 1 to 4 days after injection of the bioconjugate and FIG. 12B shows the biodistribution 5 to 7 days after injection.

Figure 13:
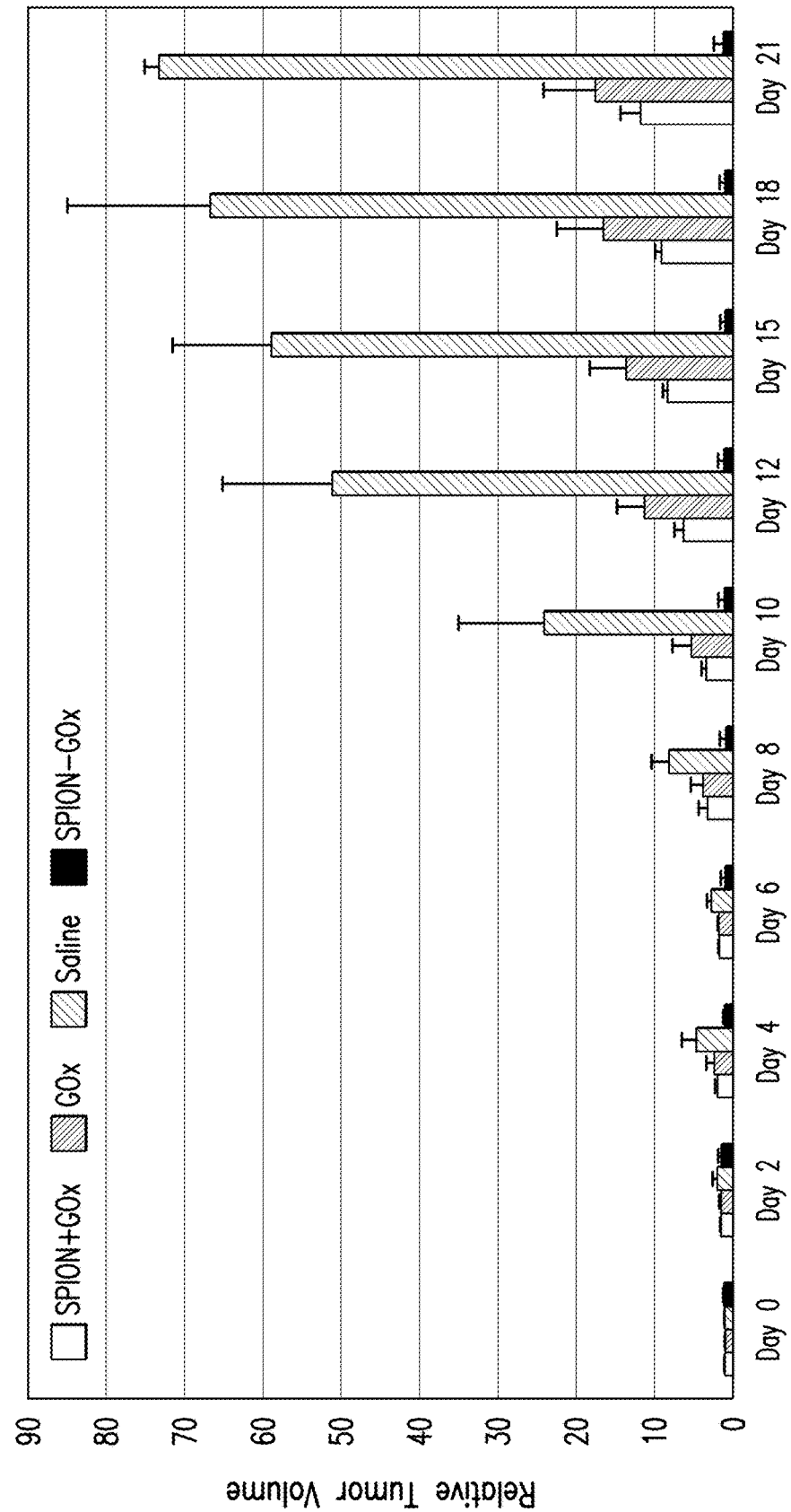

FIG. 13 provides relative tumor volumes post treatment of SPION-GOx bioconjugates compared to control agents in a xenograft model. In each dataset, the first column represents the group treated with unconjugated mixing of SPION and GOx; the second column represents the group treated with GOx alone; and the third column represents the control group that was treated with saline; the fourth column represents the group treated with SPION-GOx.

5. DETAILED DESCRIPTION OF THE INVENTION

The presently disclosed subject matter relates to bioconjugates of glucose oxidase (GOx) and nanoparticles, such as superparamagnetic iron oxide nanoparticles (SPION), that optionally further include a targeting probe, such as an antibody, protein, small molecule, or peptide. The bioconjugates can selectively target tumor cells and cause cell death by converting blood glucose into reactive oxygen species (ROS) by way of hydrogen peroxide. In particular, the GOx can catalyze the oxidation of beta-D-glucose to D-gluconolactone, releasing hydrogen peroxide as a byproduct. The conjugated nanoparticles can catalyze the degradation of hydrogen peroxide to ROS. In embodiments with SPION, MRI can be used to assist and confirm the specific delivery of the bioconjugates to tumor cells through intrinsic MRI guidance.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of", and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "bioconjugate" or "conjugate" refers to two or more components joined by a covalent bond, in which at least one of the components is a biomolecule such as an enzyme, protein or antibody. For example, the presently disclosed bioconjugates can include nanoparticles covalently joined to glucose oxidase.

As used herein, the phrase "reactive oxygen species" or the term "ROS" includes oxygen-containing, reactive chemical species. Examples of reactive oxygen species or ROS include singlet oxygen ($O_2$), superoxide anions ($.O_2^-$), and hydroxyl radicals ($.OH$).

As used herein, an "effective amount" refers to an amount of the bioconjugate that is able to generate a sufficient amount of ROS to cause cell death in a tumor cell. For example, cell death can occur by apoptosis, necrosis, or autophagy. An "effective amount" can depend upon the context in which it is being applied, and can be based on several factors, including the size of the tumor to be treated, levels of blood glucose, and the duration of the treatment.

A subject can be a human or a non-human animal, for example, but not by limitation, a non-human primate, a dog, a cat, a horse, a rodent, a cow, a goat, a rabbit, etc.

A "method of treating" a tumor cell or a tumor or a cancer or a subject having a cancer or a subject having a tumor is a method that achieves one or more of a reduction in tumor growth rate, a reduction in tumor growth, a reduction in tumor volume, a reduction in metastatic dispersal of the tumor/cancer, an improvement in quality of life and/or a prolongation of survival of a subject.

For clarity of description, and not by way of limitation, the detailed description of the presently disclosed subject matter is divided into the following subsections:
(1) bioconjugates;
(2) methods of making bioconjugates;
(3) methods of treatment;
(4) pharmaceutical compositions; and
(5) kits.

5.1. Bioconjugates

The presently disclosed subject matter relates to bioconjugates of glucose oxidase (GOx) and nanoparticles, such as superparamagnetic iron oxide nanoparticles (SPION). In certain embodiments, the bioconjugates can further include a targeting probe, such as an antibody, small molecule, protein, or peptide, to specifically target tumor cells. The bioconjugates can include GOx and nanoparticles in a ratio of from about 0.01:1 to about 100:1.

GOx is a well-characterized enzyme that catalyzes the oxidation of beta-D-glucose to D-gluconolactone while releasing hydrogen peroxide ($H_2O_2$) as a byproduct. This reaction effectively consumes glucose and exhibits significant activity against harmful organisms due to the generated hydrogen peroxide. As such, GOx can be used as a digestive support to provide various health benefits. For example, GOx derived from *Aspergillus niger* has been approved by the FDA as a food and beverage additive. For targeting and destroying tumor cells, it was found that hydrogen peroxide from the reaction of GOx and glucose could be further catalyzed to reactive oxygen species (ROS), including singlet oxygen ($O_2$), superoxide anions ($.O_2^-$), and hydroxyl radicals ($.OH$), that are effective in causing cell death in tumor cells.

Thus, in certain non-limiting embodiments, GOx can be conjugated to nanoparticles, such as iron oxide nanoparticles, that are able to catalyze the degradation of hydrogen peroxide to ROS. Such a GOx-nanoparticle bioconjugate can thereby produce ROS by consuming blood glucose and can be suitable for cancer treatment by targeting and destroying tumor cells.

Figure 1:
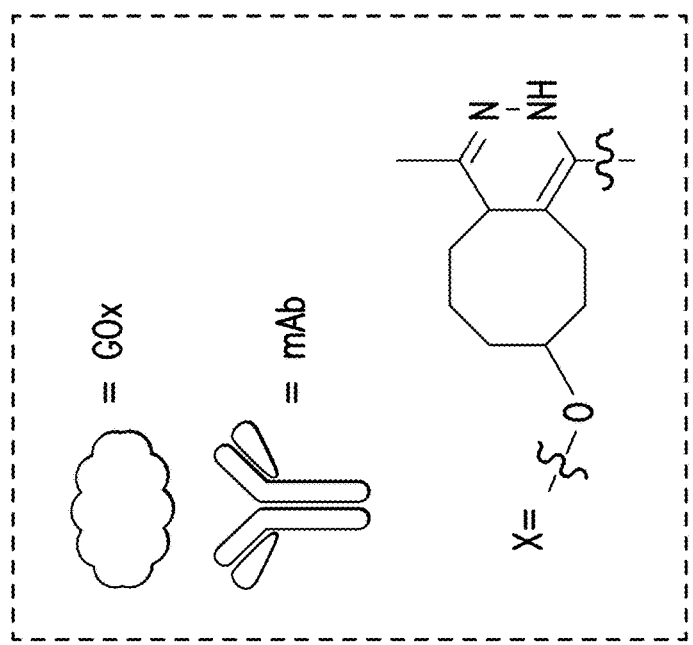
FIG. 1 is a schematic illustration of the structure of a mAb-GOx-SPION bioconjugate in accordance with certain non-limiting embodiments of the presently disclosed subject matter.
Figure 1:
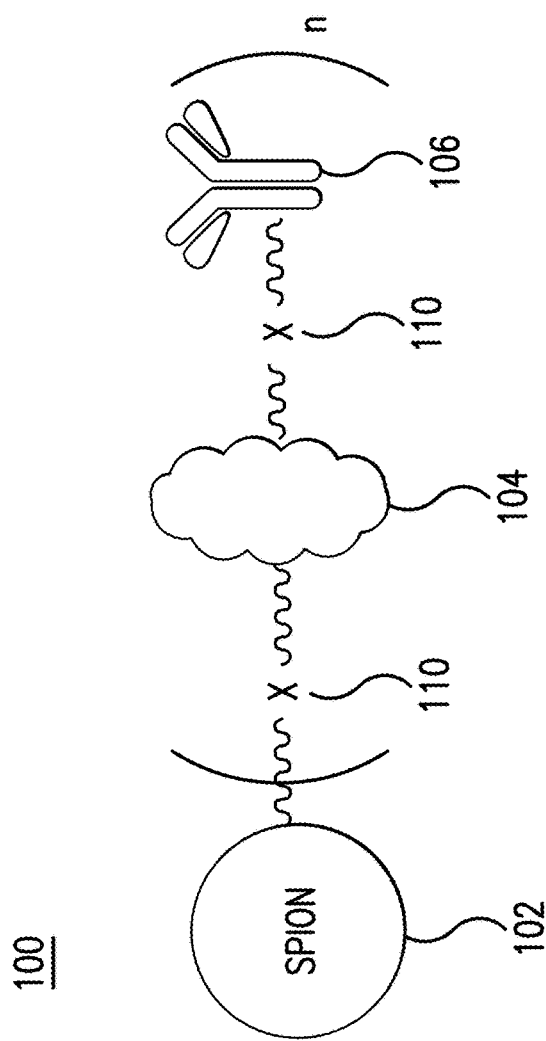
Figure 2:
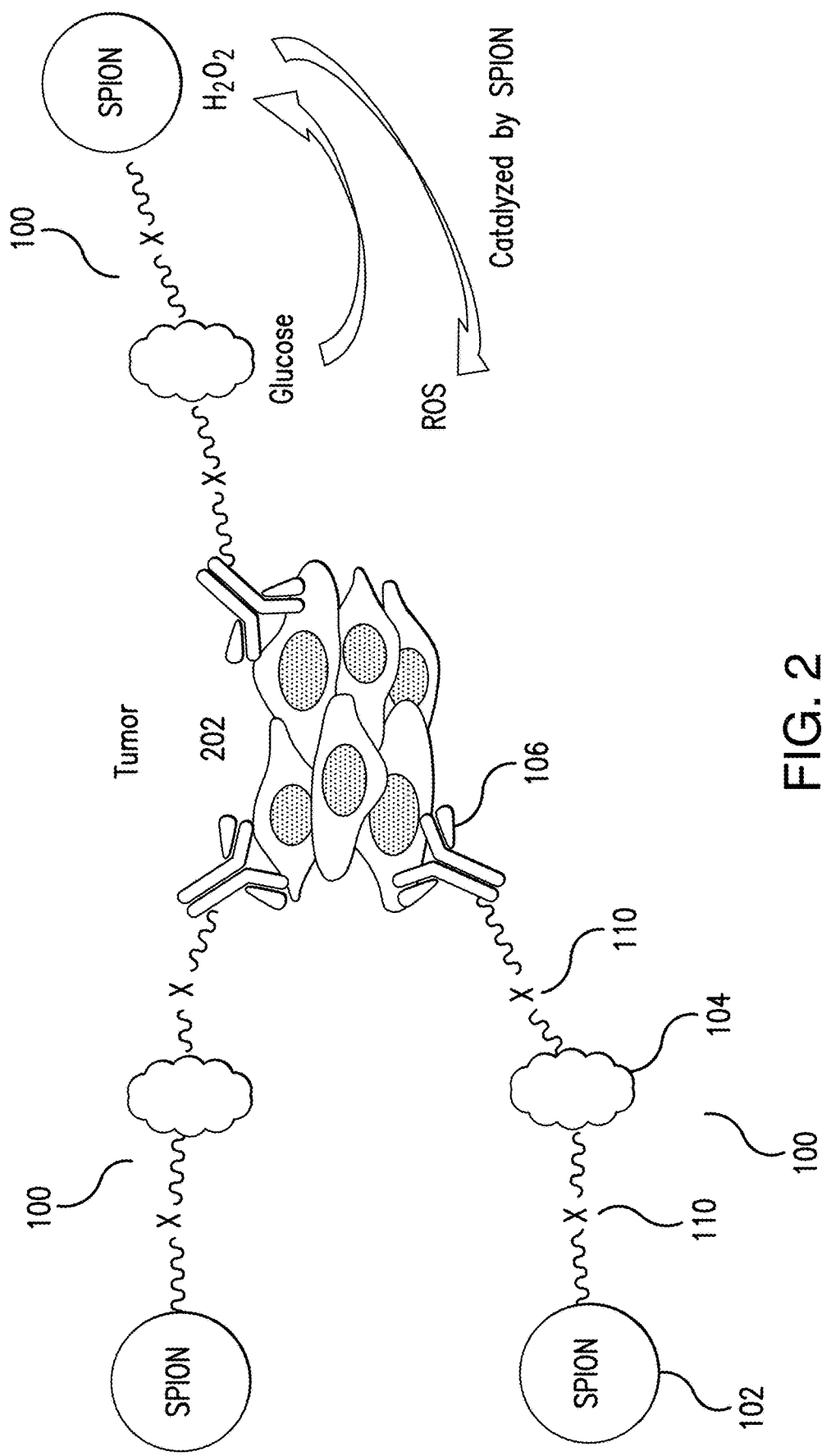
FIG. 2 is a schematic illustration of targeted destruction of tumor cells by using the mAb-GOx-SPION bioconjugate of FIG. 1.

For the purpose of illustration, and not limitation, FIG. 1 schematically illustrates a bioconjugate in accordance with the presently disclosed subject matter. As shown in FIG. 1, a GOx molecule 104 can be conjugated to a nanoparticle 102 to form a bioconjugate 100. The bioconjugate 100 can further include a targeting probe 106, such as an antibody. The GOx molecule 104 and/or the targeting probe 106, if present, can be separated from the nanoparticle using one or more spacers 110, such as polyethylene glycol, (PEG)n. FIG. 2 further illustrates, for the purpose of example and not limitation, the targeting of tumor cells using such bioconjugates 100. As shown in FIG. 2, the targeting probe 106 can bind the bioconjugate 100 to cells within a tumor 202. The GOx 104 can consume glucose to produce hydrogen peroxide, which can then be catalyzed to ROS by the nanoparticle 102.

With further reference to FIG. 2, the mechanism by which the tumor cells are destroyed can be briefly described as follows. Aggressive tumor cell proliferation can induce elevated glucose concentration within the tumor. When the glucose within the tumor comes into contact with the GOx 104 of the bioconjugate 100, it is oxidized to gluconolactone while releasing hydrogen peroxide ($H_2O_2$). $H_2O_2$ diffuses to the surface of nanoparticle 102, which catalyzes the production of ROS from $H_2O_2$. For example, in the case of iron oxide nanoparticles, such as SPION, $H_2O_2$ can be degraded to ROS by Fenton's reaction. The resulting high levels of ROS can cause tumor cell destruction, which can be used in methods of treating cancer having relatively low side-effects and long-term effectiveness. Both GOx and iron oxide nanoparticles serve as catalysts rather than reactants and, therefore, they are not consumed during the production of ROS. In particular, GOx and iron oxide nanoparticles can have a synergistic effect when conjugated in order to produce ROS. Additionally, the GOx-iron oxide nanoparticle conjugates can turn a necessary nutrient (glucose) required for tumor proliferation into a cytotoxin that destroys tumor cells, consequently synergizing the anticancer effects between tumor starving-therapy and ROS-therapy. Moreover, as described further below, the use of SPION can allow MRI to be used to assist and confirm the specific delivery of the bioconjugates to tumor cells through intrinsic MRI guidance.

The bioconjugates of the presently disclosed subject matter are able to destroy tumor cells through specific binding and in situ production of ROS. Unlike other ROS-mediated cancer therapies, the presently disclosed bioconjugates and methods require only blood glucose as the reactant for production of ROS, thereby transforming a nutrient required for tumor proliferation into a cytotoxin that destroys the tumor cells. The cytotoxic effect increases as the glucose concentration is elevated, suggesting an intrinsic feedback loop that can be managed to inhibit tumor growth that requires an increased glucose uptake.

5.1.1. Nanoparticles

In certain aspects, the presently disclosed bioconjugates include nanoparticles. For the purpose of example, and not limitation, the nanoparticles can optionally be magnetic or paramagnetic. The nanoparticles can have a diameter of from about 1 nm to about 300 nm, or from about 1 nm to about 250 nm, or from about 1 nm to about 200 nm, or from about 1 nm to about 150 nm, or from about 1 nm to about 100 nm, or from about 1 nm to about 50 nm, or from about 1 nm to about 20 nm, or from about 2 nm to about 10 nm, or from about 4 nm to about 8 nm.

The nanoparticles can be able to catalyze the degradation of hydrogen peroxide to ROS, such as singlet oxygen ($O_2$), superoxide anions ($.O_2^-$), and hydroxyl radicals ($.OH$). The nanoparticles can comprise a catalytic agent, alone or together with one or more non-catalytic substances.

In certain non-limiting embodiments, the nanoparticles can comprise a catalytic agent that is an iron oxide. As embodied herein, the iron oxide can contain an $Fe^{2+}$ and/or an $Fe^{3+}$ cation, e.g., iron (II) oxide, iron (III) oxide, and mixed oxides of $Fe^{2+}$ and $Fe^{3+}$, such as magnetite. Iron oxide is able to catalyze the degradation of hydrogen peroxide to ROS via Fenton's reaction. For example and not limitation, the nanoparticles can be superparamagnetic iron oxide nanoparticles (SPION). The use of SPION has been approved by FDA for clinical applications. Due to its superparamagnetism, SPION can advantageously be used to guide magnetic resonance imaging (MRI). To-date, SPION has been widely used and studied for targeted delivery of drugs, tissue engineering, targeted destruction of tumor tissue through hyperthermia, magnetic transfections, and chelation therapy.

SPION generally contains a magnetite ($Fe_3O_4$) core. The superparamagnetic property of $Fe_3O_4$ nanoparticles can be manipulated provide MRI guidance. When used therapeutically, SPION is typically encapsulated by a thin film of silica and as such, the $Fe_3O_4$ is not in direct contact with the outside environment and the surface chemical properties of $Fe_3O_4$ have not yet been explored for biomedical applications. However, in the presently disclosed subject matter, the SPION can be uncoated. It has been found that uncoated $Fe_3O_4$ nanoparticles have an intrinsic peroxidase-like activity, which can be used to catalyze the production of ROS from $H_2O_2$, similarly to horseradish peroxidase (HRP). For example, $Fe_3O_4$ nanoparticles have been previously shown to catalyze color reaction of 3,3,5,5-tetramethylbenzidine (TMB) in the presence of hydrogen peroxide, and have been used to construct a magnetite nanoparticle-linked immunoassay by replacing the HRP used in conventional enzyme-linked immunosorbent assay (ELISA) with $Fe_3O_4$ nanoparticles (see Gao L Z, Wu J, Lyle S., Zeihr K, Cao L L, Gao D. Magnetite Nanoparticle-Linked Immunosorbent Assay, Journal of physical chemistry C. 2008; 112:17357-17367, the contents of which are hereby incorporated by reference in their entirety).

In the presently disclosed subject matter, either coated or uncoated SPION can be used and conjugated with GOx. In certain embodiments, the conjugation of GOx and SPION provides a synergistic effect that is not present when these components are not conjugated, permitting the bioconjugate to facilitate the production of ROS from blood glucose. Thus, the GOx-SPION bioconjugate can simultaneously perform two functions. First, the synergy between the SPION and GOx can catalyze the production of ROS from blood glucose. Second, the SPION within the bioconjugate can provide MRI guidance, which facilitates imaging-guided drug delivery and lays the ground for a "theranostic" (combination of diagnostics and therapy) platform. Accordingly, MRI guidance can be used assist and confirm the delivery of the bioconjugate to tumor cells. In addition, as described in further detail below, the GOx-SPION conjugate can optionally be functionalized with one or more targeting probes to provide the therapy with tumor specificity.

5.1.2. Targeting Probes

In certain aspects of the presently disclosed subject matter, the GOx-nanoparticle bioconjugate can be functionalized with targeting probes that can target and bind to tumor cells to provide the therapy with tumor specificity. Any suitable targeting probe can be used, as known in the art. Such suitable targeting probes include, but are not limited, to small molecules, proteions, peptides, and antibodies (including molecules comprising antibody fragments and single chain antibodies), as are known in the art. In particular embodiments, the targeting probe is a monoclonal antibody, for example a monoclonal antibody or antibody fragment directed to a tumor specific or tumor selective antigen. In certain non-limiting embodiments, the targeting probe is a peptide, for example a peptide that selectively or specifically binds to a receptor expressed on tumor. In certain non-limiting embodiments, the targeting probe is a small molecule, for example a small molecule that selectively or specifically binds to a biomarker on a tumor. In certain non-limiting embodiments, the targeting probe specifically binds to an EGFR receptor, an integrin receptor, and/or a chemokine receptor, or a fragment thereof. For the purpose of example, and not limitation, Table 1 provides a list of targeting probes in accordance with the presently disclosed subject matter.

TABLE 1

Example targeting probes

| Biomarkers | monoclonal antibody | peptide (or small molecule) ligand |
|---|---|---|
| Integrin α4β1 | N/A | LLP2A (peptide) |
| uPAR | N/A | AE105 (peptide) |
| gastrin-releasing peptide (GRP) | N/A | BBN(7-14) (peptide) |
| SSTR2 | N/A | Tyr(3)-octreotate (peptide) |
| Folate receptor | N/A | Folic acid (small molecule) |
| CCR5 | N/A | DAPTA (peptide) |
| CXCR4 | UMB2 (ab124824) | AMD 3100, AMD 3465 (small molecules), T140, CPCR4-2 (peptides), ubiquitin (protein) |
| Integrin αvβ3 | Etaracizumab | RGD (peptide) |
| Plectin-1 | E398P (ab32528) | PTP (peptide) |
| EGFR | Cetuximab | Erlotinib (small molecule) |
| VEGF | Bevacizumab | N/A |
| MUC4 | mAb 8G7 | N/A |
| CA19-9 | 1116NS19-9 | N/A |
| CD40 | CP-870,893 | N/A |
| PD-11 | Atezolizumab | N/A |
| CD90 | ab92574 | N/A |

In certain non-limiting embodiments, the targeting probe can be conjugated to the GOx such that the GOx is sandwiched between the nanoparticle and the targeting probe. Alternatively, the targeting probe can be conjugated elsewhere on the GOx-nanoparticle bioconjugate, e.g., the nanoparticle can be sandwiched between the GOx and the targeting probe.

As embodied herein, the targeting probe can be specific to one or more components of a tumor cell. In certain non-limiting embodiments, the targeting probe can be specific to a biomarker on the tumor cell. For example, in particular embodiments, the targeting probe can be specific to the epidermal growth factor receptor (EGFR), which is overexpressed in tumor cells. As such, the targeting probe can selectively bind to tumor cells while having only limited interactions with normal cells that do not overexpress the biomarker. By selectively targeting tumor cells using a targeting biomarker, the bioconjugates can be highly efficient in destroying tumor cells while having minimal cytotoxicity on healthy cells.

For example, and not limitation, the biomarker can be selected from epidermal growth factor (EGFR), integrin α1β1, integrin α2β1, integrin α3β1, integrin α4β1, integrin α5β1, integrin α6β1, integrin αvβ3, uPAR, gastrin-releasing peptide (GRP), SSTR2, SSTR3, SSTR4, SSTR5, Folate receptor, CCR2, CCR5, CXCR4, plectin-1, VEGF, CA19-9, PD-I1, Her2/neu, 5-alpha reductase, α-fetoprotein, AM-1, APC, APRIL, BAGE, β-catenin, Bc12, bcr-abl (b3a2), CA 125, CASP-8/FLICE, Cathepsins, CD19, CD20, CD21, CD23, CD22, CD38, CD33, CD35, CD40, CD44, CD45, CD46, CD5, CD52, CD55, CD59 (791Tgp72), CDC27, CDK4, CEA, c-myc, COX-2, Cytokeratin, DCC, DcR3, E6/E7, EGFR, EMBP, Ena78, Estrogen Receptor (ER), FGF8b and FGF8a, FLK 1/KDR, G250, GAGE-Family, gastrin 17, Gastrin-releasing hormone (bombesin), GD2/GD3/GM2, GnRH, GnTV, gp100/Pme117, gp-100-in4, gp15, gp75/TRP-1, hCG, Heparanase, Her3, HMTV, Hsp70, hTERT (telomerase), IGFR1, IL 13R, iNOS, Ki 67, KIAA0205, K-ras, H-ras, N-ras, KSA (CO17-1A), LDLR-FUT, MAGE Family (MAGE1, MAGE3, etc.), Mammaglobin, MAP17, Melan-A/MART-1, mesothelin, MIC A/B, MT-MMP's, such as MMP2, MMP3, MMP7, MMP9, Mox1, Mucin, such as MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, Progesterone Receptor (PR), PSA, PSM, RAGE-1, Rb, RCAS1, SART-1, SSX gene family, STAT3, STn (mucin assoc.), TAG-72, TGF-α, TGF-β, Thymosin β-15, IFN-γ, TPA, TPI, TRP-2, Tyrosinase, VEGF, ZAG, p16INK4, Myo D1, Glutathione, and S-transferase.

For illustration, FIG. 1 illustrates a mAb-GOx-SPION bioconjugate in which a monoclonal antibody is used as the targeting probe. As shown in FIG. 1, GOx 104 can be sandwiched between SPION 102 and mAb 106. Alternatively, the SPION can be sandwiched between GOx and mAb. As further illustrated in FIG. 2, the antibody of the mAb-GOx-SPION can bind to tumor cells and thereby bring the GOx and SPION into proximity with the tumor cells. As will be described in greater detail below, the proximity of the GOx and/or SPION can be controlled by the use of spacers such as polyethylene glycol.

In certain embodiments, the monoclonal antibody can be an animal (e.g., mouse) antibody, or a chimeric or humanized antibody. The monoclonal antibody can be specific to one or more receptors present within tumor cells. In particular embodiments, the monoclonal antibody can be cetuximab, which is a chimeric antibody that is specific to the epidermal growth factor receptor (EGFR). In other non-limiting embodiments, the targeting probe can be another monoclonal antibody, fragment thereof, peptide, or small molecule, such as those identified in Table 1.

In certain non-limiting embodiments, the targeting probe and/or the GOx-nanoparticle bioconjugate can be fluorescently labeled, e.g., with a fluorescent dye as known in the art. For example, in particular embodiments, the florescent dye can be a cyanine-based dye such as Cy3 or Cy7. In certain embodiments, the targeting probe can be fluorescently labeled. Additionally or alternatively, the GOx can be fluorescently labeled.

5.1.3. Additional Components

The bioconjugates of the presently disclosed subject matter can further include one or more additional components. For example, in certain embodiments, a spacer can be disposed between the various constituents of the bioconjugates. The spacer can control the reticuloendothelial system uptake by stabilizing the bioconjugate in the physiological environment. Additionally, the spacer can reinforce the conjugation between the nanoparticle, GOx, and targeting probe, if present, be used to control the relative positions of the nanoparticle and GOx.

In certain embodiments of the presently disclosed subject matter, one or more spacers can be disposed between the GOx and the nanoparticle. Alternatively or additionally, one or more spacer can be disposed between the GOx and a targeting probe. Where spacers are used between both the GOx and the nanoparticle and the GOx and the targeting probe, the spacers can be the same or different.

In certain embodiments, the spacer can comprise a polymer or a biomolecule. In certain non-limiting examples, the polymer can be polyethylene glycol, polyethylene, polyethylene glycol, dendrimers, polyacrylic acid, hydroxyethyl starch (HES), poly lactide-co-glycolide, poly-D, L-p-dioxanonepoly lacticacid-ethylene glycol block copolymer (PLA-DX-PEG), poly(ortho) esters, poly-glutamate, polyaspartates, polymer of α-β-unsaturated monomers such as (meth)acrylic acid, crotonic acid, maleic acid, maleic anhydride, fumaric acid, itaconic acid/anhydride, etc., comonomers including vinyl ethers, vinyl esters, vinylamine amides, olefins, and/or diallyl dialkyl ammonium halides, preferably vinyl ether, poly(diethylenglycoladipat), polyethyleneimine, polyglycolide, polyurea, Polylimonen (=Polylimo), poly(2-methyl-1,3-propylene adipate), and graft polymers and graft (block) polymers, e.g., with other polymers.

For example and not limitation, polyethylene glycol (PEG)n can be used as the spacer. The PEG can have a molecular weight of from about 25,000 Da to about 100,000 Da, or from about 25,000 Da to about 50,000 Da, e.g., a molecular weight of about 200 Da, about 300 Da, about 400 Da, about 30,000 Da, about 35,000 Da, or about 40,000 Da. In particular embodiments, the polyethylene glycol spacer can include from about 1 to about 2000 PEG units.

In certain non-limiting embodiments, the size and use of a spacer can be selected to control the overall size of the bioconjugate. Thus, the size and use of a spacer can be based, at least in part, on the size of the nanoparticle used in the bioconjugate. In particular embodiments, the size of the overall bioconjugate can be controlled to induce the enhanced permeability and retention (EPR) effect such that the bioconjugates permeate and accumulate in tumor cells at a greater rate than in normal cells. By inducing EPR, the selectively of treatment using the bioconjugates of the presently disclosed subject matter can be increased to efficiently cause cell death in tumor cells.

5.2. Methods of Making Bioconjugates

The presently disclosed subject matter also relates to methods of making bioconjugates, e.g., mAb-GOx-SPION bioconjugates. For purpose of example and not limitation, the iron oxide nanoparticle and GOx can be ligated covalently, for examples via Diels-Alder ligation (e.g., TCO/Tz based ligation) or click reactions (e.g., $N_3$/alkyne), with a resulting ligation product disposed between the two components.

In certain non-limiting embodiments, the method can first include preparing the nanoparticles, e.g., SPION. For example, and with reference to FIG. 3, SPION can be synthesized through a high-temperature solution phase reaction of iron(III) acetylacetonate with an organic alcohol (ROH) in the presence of an organic acid (RCOOH) and amine ($RNH_2$). For example and not limitation, the organic alcohol can be 1,2-hexadecanediol and the iron(III) acetylacetonate can be reacted with the 1,2-hexadecanediol in the presence of oleic acid and oleylamine. The SPION can then be functionalized with amino groups, carboxylic acids, thiols, azides or other functional moieties. For example, SPION can be functionalized by exchanging the ligand on the as-synthesized SPION with aminosilane to form SPION-$NH_2$.

Figure 4:
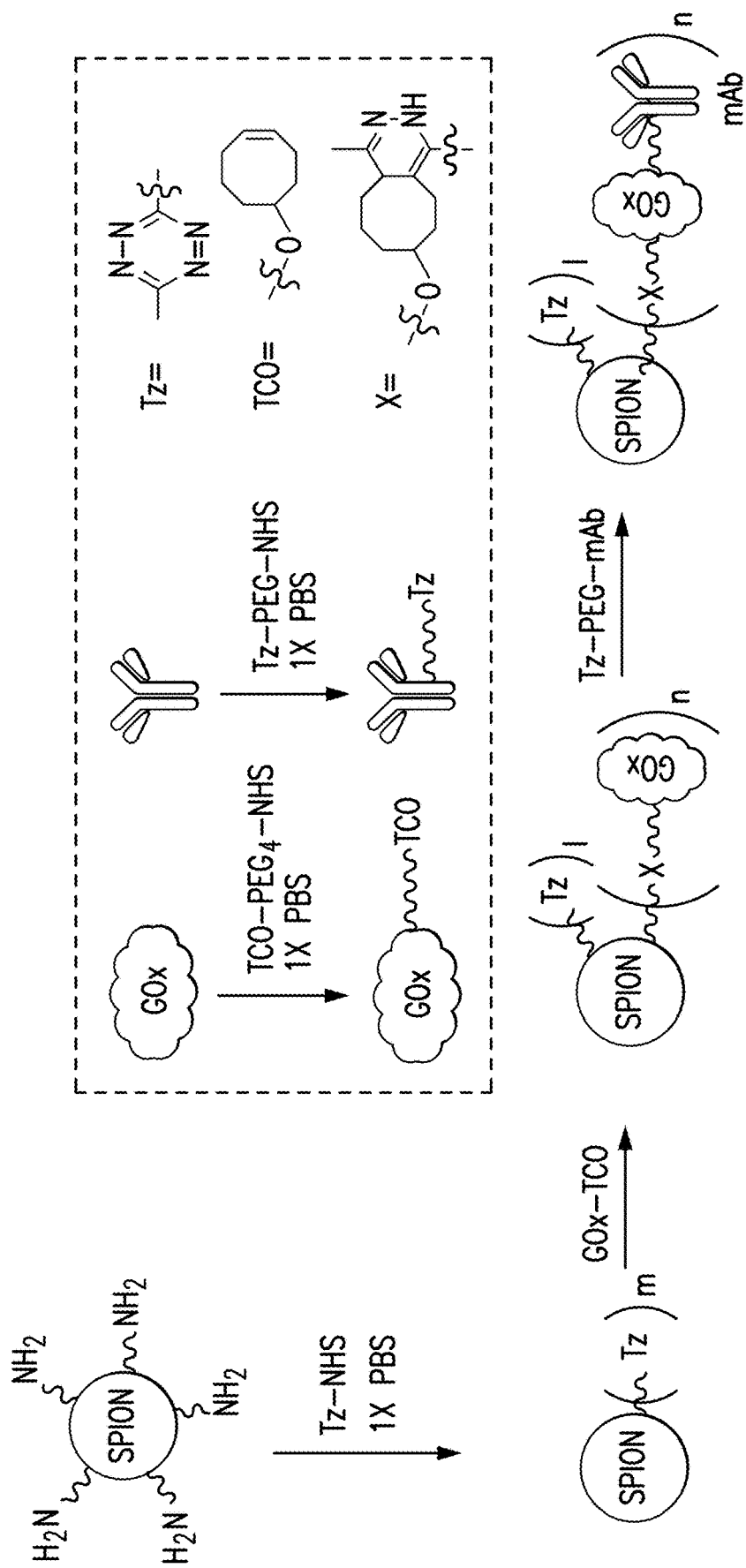
FIG. 4 is a schematic illustration of an example process for preparing a mAb-GOx-SPION bioconjugate, in accordance with certain non-limiting embodiments of the presently disclosed subject matter.

Functionalized SPION can then be further reacted to obtain bioconjugates according to the presently disclosed subject matter. For the purpose of example, and not limitation, FIG. 4 schematically shows the preparation of a mAb-GOx-SPION bioconjugate in accordance with one embodiment of the presently disclosed subject matter. As shown in FIG. 4, the SPION-$NH_2$ can be first functionalized with tetrazine using (Tz)-NHS in the presence of a buffer (e.g., PBS), resulting in SPION-$(Tz)_m$, which can be further conjugated with GOx and a monoclonal antibody.

Separately, the GOx and monoclonal antibody can be prepared for conjugation. For example, trans-cyclooctene (TCO) modified GOx (GOx-TCO) can be prepared by reacting the GOx with TCO-$PEG_4$-NHS in the presence of a buffer (e.g., PBS), where NHS is N-hydroxysuccinimide. The monoclonal antibody can be similarly prepared as a tetrazine modified antibody (mAb-Tz) by reacting the antibody with Tz-PEG-NHS in the presence of a buffer (e.g., PBS).

The GOx-TCO can be conjugated with the SPION-$(Tz)_m$ via the biorthogonal ligation between Tz and TCO to form a GOx-SPION bioconjugate. The ratio between GOx and SPION in the GOx-SPION bioconjugate can be varied from about 0.01:1 to about 100:1. In certain embodiments, the ratio between GOx and SPION in the GOx-SPION bioconjugate is from about 0.0001:1 to about 10000:1, from about 0.001:1 to about 1000:1, from about 0.01:1 to about 100:1, from about 0.02:1 to about 50:1, from about 0.05:1 to about 20:1, or from about 0.1:1 to about 10:1. This ratio can be controlled by varying the amount of GOx-TCO and SPION-$(Tz)_m$. The ratio between TCO and GOx in GOx-TCO can be varied from about 1:1 to about 1000:1. In certain embodiments, the ratio between TCO and GOx in GOx-TCO is from about 0.0001:1 to about 100000:1, from about 1:1 to about 10000:1, from about 1:1 to about 5000:1, from about 1:1 to about 1000:1, from about 1:1 to about 100:1, or from about 10:1 to about 100:1. The ratio between Tz and SPION in SPION-$(Tz)_m$ can be varied from about 1000:1 to about 1:1. In certain embodiments, the ratio between Tz and SPION in SPION-Tz is from about 0.0001:1 to about 100000:1, from about 1:1 to about 10000:1, from about 1:1 to about 5000:1, from about 1:1 to about 1000:1, from about 1:1 to about 100:1, or from about 10:1 to about 100:1.

Alternatively, SPION-TCO can be conjugated with GOx-Tz. The ratio between TCO and SPION in SPION-TCO can be varied from about 1:1 to about 1000:1. In certain embodiments, the ratio between TCO and SPION in SPION-TCO is from about 0.0001:1 to about 100000:1, from about 1:1 to about 10000:1, from about 1:1 to about 5000:1, from about 1:1 to about 1000:1, from about 1:1 to about 100:1, or from about 10:1 to about 100:1. The ratio between Tz and GOx in GOx-Tz can be varied from about 1:1 to about 100:1. In certain embodiments, the ratio between Tz and GOx in GOx-Tz is from about 0.0001:1 to about 100000:1, from about 1:1 to about 10000:1, from about 1:1 to about 5000:1, from about 1:1 to about 1000:1, from about 1:1 to about 100:1, or from about 10:1 to about 100:1.

The conjugation of GOx-TCO and SPION-(Tz)$_m$ will result in a group of Formula X being disposed between the SPION and the GOx, further separated by a spacer, as shown in FIG. 4.

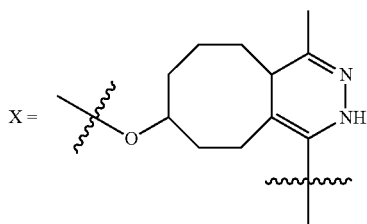 [SMILES: *OC1CCCC2C(C)=NNC(*)=C2CC1]

In certain non-limiting embodiments, the group of Formula X that is disposed between the SPION and the GOx can be a conjugation product of a pair other biorthogonal ligation moieties, e.g., a first biorthogonal ligation moiety and a corresponding second biorthogonal ligation moiety. Examples of biorthogonal ligation moieties include, but are not limited to, trans-cyclooctene, tetrazine, cyclooctyne, alkyne, azide, alkene, tetrazole, photo-DIBO and cyclopropenones. As embodied herein, photo active moieties can be the precursor of tetrazole and/or photo-DIBO. The combination of biorthogonal moieties can be selected based on the needs of the target.

Similarly, the targeting probe, e.g., mAb-Tz, can be conjugated to GOx-SPION bioconjugate via the same biorthogonal ligation between the TCO on the GOx and the Tz on the antibody, resulting in the mAb-GOx-SPION bioconjugate. The GOx and antibody can be separated by PEG spacers. For example, biorthogonal ligation between the TCO on the GOx and the Tz on the antibody can result in another group of Formula X being disposed between the GOx and the antibody. In certain embodiments the targeting probe can be conjugated to the GOx or the SPION prior to the conjugation between the GOx and the SPION.

A person of skill in the art will appreciate that although the disclosed method was described with referent so a SPION nanoparticle and a monoclonal antibody targeting probe, similar techniques can be used to conjugate other nanoparticles and targeting probes with GOx.

In certain non-limiting embodiments, the conjugation between the nanoparticles and the GOx and/or the targeting probe and the GOx or nanoparticles can be prepared by a different reaction scheme, as known in the art. Examples of suitable reactions include, but are not limited to, Diels-Alder reactions, azide-alkyne based click reactions (e.g., Cu(I) catalyzed azide-alkyne cycloaddition and metal-free azide-alkyne cycloadditions), Staudinger ligation, thiol-maleimide addition, oxime ligation, and thiol-ene reactions.

5.3. Methods of Treatment

The presently disclosed subject matter also relates to methods of treating tumor cells, or a subject having a cancer, using GOx-nanoparticle bioconjugates. For example, such methods can include administering to a subject an effective amount of GOx-nanoparticle bioconjugates to cause tumor cell death, e.g., by apoptosis, necrosis, or autophagy. As embodied herein, cell death can be facilitated by the ROS produced during the degradation of the hydrogen peroxide that is formed by GOx during the oxidation of beta-D-glucose. As described previously, the degradation of hydrogen peroxide can be catalyzed by the nanoparticles, e.g., SPION.

In certain embodiments, the GOx and nanoparticles can be administered separately and conjugated in vivo. For example, nanoparticles such as SPION can be introduced to the subject and MRI guidance can be used to deliver the SPION to a specific tumor. In certain embodiments, SPION can be introduced to the bloodstream parenterally, for example, via an intravenous or intramuscular infusion. MRI can then be used to track and guide the SPION to the tumor. Subsequently, GOx can be administered to the subject in order to form a bioconjugate with the SPION that has already been guided to the appropriate location. Administration and conjugation of GOx can initiate production of ROS. In certain embodiments, the SPION can be functionalized, for example, with amino groups or tetrazine, as described above, prior to administration. Similarly, the GOx can also be functionalized, for example with trans-cyclooctene, prior to administration. As such, the SPION and GOx can be primed to conjugate when they are both present at the site of the tumors. Additionally, by delaying the conjugation of the GOx and SPION until they are in place proximate the tumor cells, ROS will only be generated in the vicinity of the tumor cells for efficient treatment of the tumor cells. Both GOx and SPION serve as catalysts but not reactants and, therefore, they are not consumed during production of ROS. In certain non-limiting embodiments, the GOx-SPION bioconjugates do not contain a targeting probe. In certain non-limiting embodiments, the GOx-SPION bioconjugates contain a targeting probe that is attached on either GOx or SPION through a biorthogonal ligation.

Alternatively, in other embodiments of the presently disclosed subject matter, the bioconjugates can be prepared prior to administration to the subject. For example, GOx and a nanoparticle, e.g., SPION, can be conjugated, optionally with a targeting probe, as described above. The assembled bioconjugates can then be administered to a patient. For example, the bioconjugates can be administered parenterally, e.g., intravenously or intramuscularly.

In certain non-limiting embodiments, MRI guidance of the SPION core can be used to guide the delivery of the assembled bioconjugates to the appropriate location, e.g., to the tumor cells. For example, in certain embodiments, MRI can be used in image-guided delivery of the bioconjugates. Alternatively or additionally, a magnetic field can be used to manipulate and localize the bioconjugates to the appropriate location within a subject, e.g., to the tumor cells. The use of a magnetic field to localize delivery of the bioconjugates can be used to improve the specificity and effectiveness of the bioconjugates in targeting tumor cells, either in conjunction with or as an alternative to the use of a targeting probe on the bioconjugates.

Thus, the GOx-nanoparticle bioconjugates of the presently disclosed subject matter can be used as new treatments for tumor cells. The bioconjugates of the presently disclosed subject matter can be specifically targeted to tumor cells, for example, using MRI guidance or with the assistance of a targeting probe with high specificity for tumor cells. Additionally, the bioconjugates of the presently disclosed subject matter were found to have minimal cytotoxic effects on normal cells, e.g., cells that do not overexpress EGFR. As a result, treatment of cancer using these non-invasive techniques can have minimal adverse side-effects.

Additionally, because the GOx and nanoparticles act as catalysts to the production of ROS, they are not consumed. Further, the GOx-nanoparticle bioconjugates have a relatively long half-life and can generate GOx over long periods of time. Thus, treatment with the bioconjugates of the presently disclosed subject matter can provide persistent, long-term effectiveness. Thus, in certain non-limiting embodiments, the bioconjugates can be administered to a subject on a weekly, biweekly, or monthly basis.

Further, due to their long-term effectiveness and high specificity, the GOx-nanoparticle bioconjugate of the presently disclosed subject matter has the advantage of permitting the use of relatively low or lower therapeutic doses relative to agents with shorter durations of action and/or lower specificity. In certain non-limiting embodiments, an adult subject can receive a dose of from about 0.01 mg Fe/kg to about 100 mg Fe/kg. In certain non-limiting embodiments, an adult subject can receive a dose of from about 0.01 mg Fe/kg to about 50 mg Fe/kg, from about 0.1 mg Fe/kg to about 10 mg Fe/kg, from about 0.2 mg Fe/kg to about 8 mg Fe/kg, from about 0.2 mg Fe/kg to about 5 mg Fe/kg, from about 0.3 mg Fe/kg to about 4 mg Fe/kg, or from about 0.5 mg Fe/kg to about 2 mg Fe/kg of the bioconjugate in a single treatment. For example, and not limitation, the presently disclosed bioconjugates can be cytotoxic at very low concentrations, e.g., serum concentrations as low as about 1,000 ng/mL, as low as about 500 ng/mL, or as low as about 200 ng/mL, or as low as about 100 ng/mL.

In certain non-limiting embodiments, the course of treatment with the bioconjugates of the presently disclosed subject matter can further include lifestyle changes that enhance the effectiveness of the bioconjugates. For example, the therapeutic effectiveness of the bioconjugates can be enhanced through greater glucose consumption to increase levels of blood glucose and/or through physical exercise and respiration to increase levels of oxygen.

5.4. Pharmaceutical Compositions

The presently disclosed subject matter also relates to pharmaceutical compositions comprising the bioconjugates. Pharmaceutical compositions of this disclosure also can be administered in combination therapy, i.e., combined with other agents. In certain embodiments, the combination therapy can include a bioconjugate of the presently disclosed subject matter combined with at least one additional agent.

In certain non-limiting embodiments, the pharmaceutical compositions can be formulated for parenteral administration. For instance, the pharmaceutical compositions can be formulated for intravenous, intrathecal, pulmonary or intramuscular administration, or for local instillation into a tumor site. The pharmaceutical composition can further include a pharmaceutically acceptable carrier that is compatible with the intended route of administration. For example, the pharmaceutically acceptable carrier can be a pharmaceutically acceptable solvent, suspending agent, or vehicle for delivering the bioconjugates to the subject. In certain embodiments, solutions or suspensions used for parenteral administration can include one or more of a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes, multiple dose vials made of glass or plastic, or other packaging materials, as is known in the art. In certain embodiments, the pharmaceutical compositions can be formulated in dosage unit form, as will be understood in the art.

5.5. Kits

The presently disclosed subject matter further provides kits that can be used to practice the presently disclosed subject matter. For example, and not by way of limitation, a kit of the presently disclosed subject matter can comprise nanoparticles and GOx. In certain embodiments, a kit of the presently disclosed subject matter can optionally include instructions on how to prepare bioconjugates from the nanoparticles and GOx and/or how to administer the bioconjugates to a subject.

In certain non-limiting embodiments, in addition to nanoparticles and GOx, the kits can further include reagents for conjugating the nanoparticles, GOx, and/or the targeting probe, where present. For example, the kits can include iron(III) acetylacetonate for preparing SPION and reagents for functionalizing the SPION, such as organic alcohols (e.g., 1,2-hexadecanediol), organic acids (e.g., oleic acid), amines (oleylamine), aminosilane, and tetrazine. Alternatively, the nanoparticles can be provided in kits prepared and functionalized, as necessary for conjugation with GOx. Similarly, the GOx can be accompanied with reagents necessary to conjugate it to the nanoparticles, such as TCO-$PEG_4$-NHS. Alternatively, the GOx can be provided in kits already modified with trans-cyclooctene (TCO). The kits can further include buffers and/or solvents, as required to perform the conjugation.

In additional non-limiting embodiments, the kits can further include targeting probes. For example, the targeting probes can be monoclonal antibodies. For example, and not limitation, the kits can be provided with monoclonal antibodies that have been modified with tetrazine. Alternatively, monoclonal antibodies and Tz-PEG-NHS can be provided as separate reagents.

6. EXAMPLES

The following Examples are offered to more fully illustrate the disclosure, but are not to be construed as limiting the scope thereof.

Example 1: Preparation of mAb-GOx-SPION Bioconjugates

This Example illustrates the process for the preparation of GOx-SPION bioconjugates in accordance with the presently disclosed subject matter. This Example further provides for the functionalization of GOx-SPION with a monoclonal antibody (mAb) to make mAb-GOx-SPION bioconjugates.

All solvents and reagents were purchased from commercial sources and used without additional purifications, unless otherwise noted. The monoclonal antibody cetuximab (Erbitux, 2.0 mg/mL) was bought from ImClone Systems Incorporated (New York, NY). TCO-$(PEG)_4$-NHS and Tz- (PEG)$_4$-NHS were obtained from Fisher Scientific (Pittsburgh, PA). Cyanine3(Cy3)-NHS ester was purchased from Lumiprobe Corporation (Hallandale Beach, FL). All other chemicals and reagents were obtained from Sigma Aldrich (St. Louis, MO).

Figure 3:
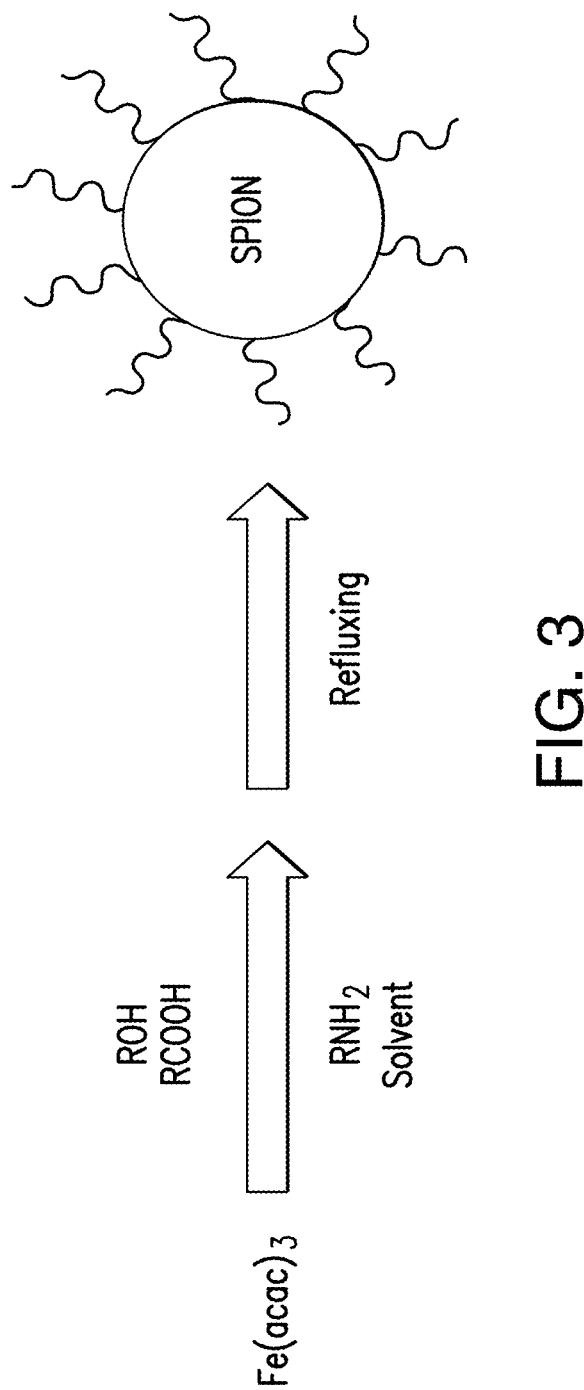
FIG. 3 is a schematic illustration of an example SPION synthesis process, in accordance with certain non-limiting embodiments of the presently disclosed subject matter.

SPION was synthesized by high-temperature solution phase reaction of iron(III) acetylacetonate with 1,2-hexadecanediol in the presence of oleic acid and oleylamine, as illustrated in FIG. 3. First, Fe(acac)$_3$ (2 mmol), 1,2-hexadecanediol (10 mmol), oleic acid (6 mmol), oleylamine (6 mmol), and benzyl ether (20 mL) were mixed and magnetically stirred under a flow of nitrogen. The mixture was heated to 200° C. for 2 h, and then heated to reflux (~300° C.) for 1 h in the nitrogen environment. After the reaction mixture was cooled to room temperature, the SPION were precipitated by adding ethanol into the mixture and washed with hexane and ethanol 3 times. The as-synthesized SPION were dispersed in hexane.

Amine-functionalized SPION (SPION-NH$_2$) was then made by exchanging the ligand on the as-synthesized SPION with aminosilane. 20 mg of SPION were dispersed in 50 mL of hexane. 0.5 mL of (3-aminopropyl)triethoxysilane was added to the SPION suspension, and the mixture was shaken for 72 h at 25° C. The resultant amino-functionalized SPION (SPION-NH$_2$) were separated using a magnet and washed with hexane 3 times. The SPION-NH$_2$ was then suspended in 20 mL of DI water.

The number of amine groups on the surface of each SPION-NH$_2$ was estimated to be around ~60 based on a fluorescamine quantification assay. FIG. 5A shows a transmission electron microscopy (TEM) image of the SPION and FIG. 5B provides a size distribution histogram. As shown in FIG. 5B, the nanoparticles were from about 4.0 nm to about 8.0 nm in diameter.

The GOx-SPION conjugate was then functionalized with cetuximab, which is an antibody that selectively binds to epidermal growth factor receptor (EGFR) and has been used in EGFR-targeted therapy. Cetuximab-GOx-SPION bioconjugate was prepared following the schematics shown in FIG. 4. Briefly, SPION-NH$_2$ was first functionalized with tetrazine (Tz)-NHS, and then conjugated with trans-cyclooctene (TCO) modified GOx (GOx-TCO) via the bioorthogonal ligation between Tz and TCO. Afterwards, cetuximab was conjugated to GOx-SPION via the same bioorthogonal ligation between TCO on GOx and Tz on cetuximab. The following describes the detailed procedure.

Cy3-cetuximab-Tz conjugate was prepared by using the following process (see FIG. 4, inset). Cy3-NHS ester (1.0 mg, 2.0 µmol) was added to a mixture of cetuximab (5.0 mL, 70 nmol) and Na$_2$HPO$_4$ buffer (0.1 M, pH=8.2, 2.0 mL), and the reaction mixture was incubated 24 h at 4° C. in darkness with gentle rotation, followed by the addition of Tz-(PEG)$_4$-NHS ester (0.25 mg, 0.5 µmol). The resulting mixture was further incubated overnight at 4° C. in darkness. The resulting Cy3-cetuximab-Tz was purified by Centricon 100 and subsequently passage over a Zeba desalting column. The concentration of purified Cy3-cetuximab-Tz was 2.0 mg/mL as determined by FPLC.

GOx-TCO conjugate was prepared by using the following procedure (see FIG. 4, inset). TCO-(PEG)$_4$-NHS ester (1.5 mg, 3.0 µmol) was added to a solution of GOx (14.6 mg, 70 nmol) in Na$_2$HPO$_4$ buffer (0.05 M, pH=8.2, 7.3 mL), and the resulting mixture was incubated overnight in a 4° C. cold room with gentle rotation. The resulting GOx-TCO conjugate was purified by Centricon 100 and subsequently passage over a Zeba desalting column. The concentration of purified azide-cetuximab was 2.0 mg/mL as was determined by FPLC.

SPION-Tz conjugate was prepared by using the following procedure. Tz-(PEG)$_4$-NHS ester (3.0 mg, 6.0 µmol) was added to a solution of the synthesized SPION (28 mg) in Na$_2$HPO$_4$ buffer (0.05 M, pH=8.2, 4.0 mL), and then the reaction mixture was incubated overnight in the 4° C. cold room with gentle rotation. The resulting SPION-Tz was isolated with a rare earth magnet and washed five times with 1×DPBS, and 20 mg of the purified SPION-Tz was obtained in 4.0 mL 1×DPBS.

SPION-GOx conjugate was prepared by using the following procedure. The above SPION-Tz (20 mg in 4 mL 1×DPBS) was mixed with the prepared GOx-TCO (2.0 mg in 1 mL 1×DPBS), and the resulting reaction mixture was incubated overnight in the 4° C. cold room with gentle rotation. The resulting SPION-GOx was isolated with a rare earth magnet and washed five times with 1×DPBS, and 15 mg of purified SPION-GOx was obtained in 3.0 mL 1×DPBS. The amount of immobilized GOx protein was estimated to be 45 µg/mL based on the Bradford protein assay.

SPION-GOx-cetuximab(Cy3) conjugate was prepared by using the following procedure. The above purified SPION-GOx (10 mg in 2 mL 1×DPBS) was mixed with the prepared Cy3-cetuximab-Tz (2.0 mg in 1 mL 1×DPBS), and the resulting reaction mixture was incubated overnight in the 4° C. cold room in darkness with gentle rotation. The resulting SPION-GOx-cetuximab(Cy3) was isolated with a rare earth magnet and washed five times with 1×DPBS, and 7.5 mg of the purified SPION-GO$_x$ was obtained in 1.5 mL 1×DPBS. The Bradford protein assay result indicated that the amount of immobilized GOx-cetuximab protein was 75 µg/mL, and the amount of immobilized cetuximab was 30 µg/mL after subtracting the immobilized GOx (45 µg/mL).

Example 2: ROS Production by GOx-SPION and mAb-GOx-SPION Bioconjugates in ROS Activity Assay The following example illustrates production of ROS by the disclosed GOx-SPION and mAb-GOx-SPION bioconjugate in an ROS activity assay.

Production of ROS by the GOx-SPION bioconjugate was characterized by using a color agent 3,3',5,5'-tetramethylbenzidine (TMB). TMB is known to be able to produce a blue color in the presence of ROS, which can be quantified by measuring the absorption at the wavelength of 650 nm. As a comparison, the levels of ROS produced by GOx and SPION alone, a mixture of GOx and SPION without conjugation, as well as the mAb-GOx-SPION bioconjugate were characterized.

The TMB-based ROS activity assay was carried out by using the following process. 20 µL SPION (5.0 mg/mL), GOx (1.0 mg/mL), a mixture of GOx (0.5 mg/mL) and SPION (2.5 mg/mL) without conjugation, GOx-SPION (5.0 mg/mL), and mAb-GOx-SPION (5.0 mg/mL) were each added into 380 µL of reaction buffer (0.1 M NaAc, pH 4, 50 µg TMB), followed by addition of either 100 µL of 100 mM glucose or 100 µL of DiH$_2$O. After the mixtures were incubated at 37° C. for 2 h, the color change was detected with a Hitachi UV-Vis spectrophotometer.

The result is presented in FIG. 6, where the peak height at 650 nm on the UV-vis absorption spectra indicates the concentration of ROS produced by the system. FIG. 6 shows that the presence of glucose in the system is essential for the production of ROS. It also shows that neither GOx nor SPION alone is able to produce ROS, even when mixed with glucose. Similarly, the mixture of unconjugated GOx and SPION in the presence of glucose was also unable to produce ROS. This result suggests that there is synergistic activity between conjugated GOx and SPION that plays an important role in the process of ROS production, as GOx is responsible for generation of hydrogen peroxide from glucose and SPION catalyzes the production of ROS from hydrogen peroxide. Unless GOx and SPION is in close proximity as in the case of a GOx-SPION bioconjugate, the intermedia product hydrogen peroxide can react with other chemical species in the system fairly quickly before it reaches the SPION and produces ROS. The result in FIG. 6 also shows that the functionalization of GOx-SPION with cetuximab does not significantly change its activity to produce ROS from glucose.

Example 3: Cytotoxicity Study of GOx-SPION in A431 Cells with High EGFR Expression The following example illustrates the cytotoxic effect of the disclosed GOx-SPION bioconjugate and the destruction of tumor cells by the GOx-SPION bioconjugate.

A431 cells with high EGFR expression were used to demonstrate tumor cell destruction by the cetuximab-GOx-SPION conjugate of Example 1. As a comparison, the A431 cells were also treated with SPION alone, a mixture of unconjugated SPION and GOx, and doxorubicin (a chemotherapy drug).

A431 cancer cells were purchased from ATCC. They were cultured in Dulbecco's Modified Eagle Medium (DMEM) containing 10% FBS, penicillin (100 U/mL), and streptomycin (100 µg/mL) at 37° C. in a humidified atmosphere containing 5% $CO_2$ and 95% air.

50 µL SPION, the mixture of GOx and SPION without conjugation, mAb-GOx-SPION, doxorubicin, or PBS (as a control) were each added to a 96-well plate seeded with A431 cancer cells, followed by addition of 100 µL of DMEM containing 4 g/L glucose. After being incubated for various amounts of time, the cells were washed with PBS 3 times. 100 µL DMEM was added before cell viability was measured by using a CellTiter-Glo viability assay kit.

Viabilities of A431 cells after different treatments are shown in FIG. 7, where 1×PBS buffer is used as the negative control (100% viability, not shown in the chart). Although treatment with 10 µg/mL cetuximab-GOx-SPION resulted in slower cell death than treatment with 50 µM (30 µg/mL) of doxorubicin, the cell viabilities of the two systems after 24 h were comparable at about 3%. In contrast, no significant reduction in the cell viability was observed after treatment with either SPION alone or mixture of unconjugated SPION and GOx after up to 24 h, with the presence of glucose in the same concentration (20 g/L).

A431 cells treated with cetuximab-GOx-SPION were examined by an in situ apoptosis detection kit (see FIG. 8) and showed typical apoptotic features, such as DNA fragmentation and nuclear condensation, indicating rapid cell death via the apoptosis pathway. The apoptosis assay was conducted by using the following procedure. A431 cells were seeded on an 8-well Permanox chamber slide at a density of 104/well. This chamber slide was then incubated (37° C., 5% CO2) for 24 h. Afterwards, the culturing medium was removed, followed by treating cells with 10 µg/mL of cetuximab-GOx-SPION and PBS as control. The slide was incubated for another 18 h.

An apoptosis detection assay was then conducted in the following procedure using an ApopTag® in situ apoptosis detection kit: (1) Aspirated the culturing medium on the chamber slide, and washed each well with PBS (pH=7.4); (2) Added in 0.2 ml/well 1% paraformaldehyde in PBS, and fixed cells for 10 min at room temperature; (3) Aspirated the solution, and washed in 2 changes of PBS for 5 min each wash; (4) Post-fixed cells in precooled ethanol:acetic acid 2:1 for 5 min at −20° C.; (5) Aspirated the solution, and washed in 2 changes of PBS for 5 min each wash; (6) Immediately applied l/well equilibration buffer directly on the specimen, and incubated for at least 10 seconds at room temperature; (7) Aspired out the buffer, and immediately pipetted onto each well 11 µl working strength TdT enzyme; (8) Incubated the specimen in a humidified chamber at 37° C. for 1 h; (9) Added in 0.2 ml/well working strength stop/wash buffer, agitated for 15 seconds, and incubated the specimen for 10 min at room temperature; (10) Washed the specimen in 3 changes of PBS for 1 min each wash; (11) Applied 13 µL/well working strength anti-digoxigenin conjugate, and incubated the specimen in a humidified chamber for 30 min at room temperature (avoided exposure to light.); (12) Washed the specimen in 4 changes of PBS for 2 min per wash; (13) Stained the specimen with 1.0 µg/mL DAPI PBS solution; (14) Washed the specimen with PBS, and applied the mounting medium; and (14) Viewed by fluorescence microscopy using standard fluorescein excitation and emission filters.

The cytotoxic effects of the system as functions of the concentrations of both cetuximab-GOx-SPION and glucose were investigated. 50 µL cetuximab-GOx-SPION (1.0 µg/mL) was added to 96-well plates seeded with A431 and HeLa cancer cells, followed by addition of 100 µL of DMEM that contains glucose at 20 g/L. After 1.5 h incubation, the cells were washed with PBS 3 times and then cultured in 200 µL of DMEM. After being incubated for another 12 h, cell viability was measured by using CellTiter-Glo viability assay kit. FIG. 9 presents cell viabilities after 1.5 h treatment with cetuximab-GOx-SPION at 4 different concentrations (0.01, 0.1, 1, and 10 µg/mL) in the presence of glucose at 2 different concentrations (4 and 20 g/L). The two different glucose concentrations were chosen to represent glucose levels found in the normal physiological environment and in tumors with significantly increased glucose uptake. The cell viability was observed to significantly decrease as the concentrations of either cetuximab-GOx-SPION or glucose increased, and the cytotoxic effect showed more dependence on the concentration of cetuximab-GOx-SPION under high levels of glucose (20 g/L) than under low levels of glucose (4 g/L), which suggests that its cytotoxic effect can be amplified where glucose update increases significantly.

Example 4: Specificity of Tumor Cell Destruction by mAb-GOx-SPION Bioconjugates in ROS Activity Assay The following example demonstrates the specificity of tumor cell destruction by the disclosed mAb-GOx-SPION bioconjugate of Example 1.

To demonstrate the specificity of tumor cell destruction by cetuximab-GOx-SPION, EGFR-overexpressed A431 and HeLa cancer cells expressing physiological levels of EGFR were treated with 1.0 µg/mL of cetuximab-GOx-SPION in the presence of 20 g/L glucose for 1.5 h, as described in Example 3. FIG. 10 shows the comparison of the cytotoxic effects on these two cancer cells. The cell viability of EGFR-overexpressed A431 cells is 45.8±8.5%, while that of HeLa cells is 91.1±7.3%, and the P value is less than 0.0001.

To visualize the specific binding of cetuximab-GOx-SPION with A431 cells, cetuximab-GOx-SPION was tagged with a fluorescent dye (Cy3 moiety) and confocal fluorescence microscopy was used to examine A431 cells after treatment with 0.1 µg/mL cetuximab(Cy3)-GOx-SPION for 1.5 h, both before and after blocking of the EGFR expressed on the cell surface. The result is shown in FIG. 11. Without blocking of EGFR, cetuximab-GOx-SPION bound to A431 cells and showed preferential distribution around the cell membrane, indicated by the intense fluorescent spots on the cell surface. In contrast, after EGFR was blocked by intact cetuximab prior to incubation with cetuximab(Cy3)-GOx-SPION, fluorescence signal was hardly detected on the cells. HeLa cells that express physiological levels of EGFR were also treated with cetuximab(Cy3)-GOx-SPION, and no appreciable fluorescence signals were observed after the same amount of incubation time. These results indicate that cetuximab-GOx-SPION bioconjugate accumulates on the EGFR-overexpressed cancer cells significantly more than on the normal cells with physiological levels of EGFR, illustrating that the binding of cetuximab-GOx-SPION to cancer cells and the destruction of the cancer cells is specific.

Example 5: Ex Vivo Biodistribution of GOx-SPION Bioconjugates in Mouse Models The following example illustrates the ex vivo biodistribution of GOx-SPION bioconjugates in mouse models.

To visualize the biodistribution of GOx-SPION within mouse models, GOx-SPION was tagged with a fluorescent dye (Cy7 moiety). 150 µg of the resulting SPION-GOx-Cy7 bioconjugate was administered to 5 mice having 4T1 breast cancer xenografts. The biodistribution of the bioconjugates was imaged at 1 day, 3 days, 4 days, 5 days, 6 days, and 7 days after injection (see FIGS. 12A-12B). As shown in FIG. 12A, at 1 day, it was found that the initial uptake of the bioconjugates was to tumor cells. Subsequently, the injection resulted in update in other locations in the body: first in the liver, then in the kidney, next in the spleen, bone and heart, and lastly in other locations, including the stomach, intestines, pancreas, and muscle tissue. However, given that initial uptake was to tumor cells, these results indicate that treatment with the bioconjugates of the presently disclosed subject matter is highly specific to tumor cells and effective to cause cell death in tumor cells.

Example 6: In Vivo Therapeutic Efficacy of Prepared SPION-GOx Conjugates

The following example illustrates the therapeutic efficacy of the disclosed SPION-GOx bioconjugate and the destruction of tumor cells by the SPION-GOx bioconjugate.

4T1 cells ($2\times10^5$ cell/mouse) were implanted subcutaneously into the right shoulders of female balb/c mice (~20 g). In vivo therapeutic efficacy experiments were performed when the tumor reached 6~8 mm in average diameter (10 days after implant). 3-5 mice were randomly assigned to 4 groups, to which the following agents were administered via tail vein injection: Group A were administered with a mixture of unconjugated SPION and GOx at the dosage of 5 mg/kg and 8.5 nmol/kg respectively; Group B were administered with GOx at the dosage of 8.5 nmol/kg; Group C were administered with 200 µL saline as control; and Group D were administered with a single dose of 5 mg/mL SPION-GOx in saline at a dosage of 5 mg/kg. All the administration was made at about the same time of the day. The size and size distribution of SPION-GOx bioconjugates were determined using DLS before injection to ensure the conjugation was complete and no precipitation was formed in the suspension. The SPION-GOx PBS solution to be used on animal study was tested using a TMB assay to verify the effective generation of ROS. The weight and health conditions of the mice were monitored daily. The tumor sizes were measured and recorded every other day in the first 12 days, and then every 3 days until 21 days post injection, at which time point the tumors were harvested. The volumes of the tumors were calculated by the following equation: $V = L \times W^2/2$.

By analyzing tumor growth rate and weight change after treatment, therapeutic efficacy of SPION-GOx bioconjugates was evaluated in 4T1 cancer cells in vivo. The reduction of tumor sizes demonstrates the antitumor effects of the ROS created by the SPION-GOx bioconjugates, while no severe side effects such as significant weight loss or death were observed. The normalized relative tumor volumes post treatment are shown in FIG. 13. A significant slowdown of tumor growth was observed in the mice treated with SPION-GOx (the fourth column in each dataset) as compared to the 3 control groups, which was consistent with the cell study results that the ROS generated from the conjugated SPION-GOx could effectively destroy cancer cells. The mice in this group did not experience any significant body weight loss during the treatment, suggesting low side effect of the SPION-GOx treatment. Unconjugated SPION and GOx (the first column in each dataset) and GOx alone (the second column in each dataset) both inhibited tumor growth to a much lesser extent in the 21-day span. Such inhibition could be explained by the fact that GOx converted glucose to $H_2O_2$ that caused oxidative stress on cancer cells. In contrast, the saline group (the third column in each dataset) had the fastest growing tumors.

The results demonstrated that the SPION-GOx bioconjugates could effectively accumulate at tumor site and release ROS to destruct cancer cells with minimal side effect. These results indicated that treatment based on SPION-GOx bioconjugates can become novel cancer therapy.

Accordingly, these Examples demonstrate that the GOx-nanoparticle bioconjugates of the presently disclosed subject matter are able to destroy tumor cells through specific binding and in situ production of ROS. Distinguishable from other ROS-mediated therapies, treatment with these bioconjugates requires only blood glucose as the reactant for production of ROS, and turns a nutrient required for tumor proliferation into a cytotoxin that destroys the tumor cells. Moreover, these Examples show that the cytotoxic effect increases as the glucose concentration is elevated, suggesting an intrinsic feedback loop that can be managed to inhibit tumor growth requiring an increased glucose uptake. Additionally, these Examples illustrate that production of ROS and cell death is induced when SPION and GOx are conjugated.

Thus, these GOx-nanoparticle bioconjugates can be used in the development of a therapy with unprecedented low-side effect and specificity for tumor cells. Because SPION provides intrinsic MRI guidance, the SPION delivery process can be guided and confirmed by MRI to provide imaging-guided drug delivery and a theranostic (combination of diagnostics and therapy) platform.

7. REFERENCES

1. Droge, W. Physiol. Rev. 2002, 82, 47-95.
2. Apel, K.; Hirt, H. Annu. Rev. Plant Biol. 2004, 55, 373-399.
3. Valko, M.; Leibfritz, D.; Moncol, J.; Cronin, M. T. D.; Mazur, M.; Telser, J. Int. J. Biochem. Cell Biol. 2007, 39, 44-84.
4. Finkel, T. The Journal of Cell Biology 2011, 194, 7-15.
5. Fiers, W.; Beyaert, R.; Declercq, W.; Vandenabeele, P. Oncogene 1999, 18, 7719-7730.
6. Kannan, K.; Jain, S. K. Pathophysiology 2000, 7, 153-163.
7. Matés, J. M.; Sánchez-Jiménez, F. M. The International Journal of Biochemistry & Cell Biology 2000, 32, 157-170.
8. Kamata, H.; Honda, S.; Maeda, S.; Chang, L. F.; Hirata, H.; Karin, M. Cell 2005, 120, 649-661.
9. Ozben, T. Journal of Pharmaceutical Sciences 2007, 96, 2181-2196.
10. Dewey, W. C.; Ling, C. C.; Meyn, R. E. International Journal of Radiation Oncology•Biology•Physics 1995, 33, 781-796.
11. Trachootham, D.; Alexandre, J.; Huang, P. Nat Rev Drug Discov 2009, 8, 579-591.
12. Dearnaley, D. P.; Khoo, V. S.; Norman, A. R.; Meyer, L.; Nahum, A.; Tait, D.; Yarnold, J.; Horwich, A. The Lancet 1999, 353, 267-272.
13. Peeters, K. C. M. J.; van de Velde, C. J. H.; Leer, J. W. H.; Martijn, H.; Junggeburt, J. M. C.; Kranenbarg, E. K.; Steup, W. H.; Wiggers, T.; Rutten, H. J.; Marijnen, C. A. M. Journal of Clinical Oncology 2005, 23, 6199-6206.
14. Shafiq, J.; Barton, M.; Noble, D.; Lemer, C.; Donaldson, L. J. Radiotherapy and Oncology 2009, 92, 15-21.
15. Barnett, G. C.; West, C. M. L.; Dunning, A. M.; Elliott, R. M.; Coles, C. E.; Pharoah, P. D. P.; Burnet, N. G. Nat Rev Cancer 2009, 9, 134-142.
16. Dolmans, D. E. J. G. J.; Fukumura, D.; Jain, R. K. Nat Rev Cancer 2003, 3, 380-387.
17. Pass, H. I. Journal of the National Cancer Institute 1993, 85, 443-456.
18. Castano, A. P.; Mroz, P.; Hamblin, M. R. Nat Rev Cancer 2006, 6, 535-545.
19. Kashtan, H.; Haddad, R.; Yossiphov, Y.; BarOn, S.; Skornick, Y. Dis Colon Rectum 1996, 39, 379-383.
20. Brown, S. B.; Brown, E. A.; Walker, I. The Lancet Oncology 2004, 5, 497-508.
21. Allison, R. R.; Downie, G. H.; Cuenca, R.; Hu, X.-H.; Childs, C. J. H.; Sibata, C. H. Photodiagnosis and Photodynamic Therapy 2004, 1, 27-42.
22. Gatenby, R. A.; Gillies, R. J. Nat Rev Cancer 2004, 4, 891-899.
23. Kim, J.-w.; Dang, C. V. Cancer Research 2006, 66, 8927-8930.
24. Sun, S. H.; Zeng, H.; Robinson, D. B.; Raoux, S.; Rice, P. M.; Wang, S. X.; Li, G. X. J Am Chem Soc 2004, 126, 273-279.
25. Harris, M. The Lancet Oncology 2004, 5, 292-302.
26. Jonker, D. J.; O'Callaghan, C. J.; Karapetis, C. S.; Zalcberg, J. R.; Tu, D. S.; Au, H. J.; Berry, S. R.; Krahn, M.; Price, T.; Simes, R. J.; Tebbutt, N. C.; van Hazel, G.; Wierzbicki, R.; Langer, C.; Moore, M. J. New England Journal of Medicine 2007, 357, 2040-2048.
27. Karapetis, C. S.; Khambata-Ford, S.; Jonker, D. J.; O'Callaghan, C. J.; Tu, D.; Tebbutt, N. C.; Simes, R. J.; Chalchal, H.; Shapiro, J. D.; Robitaille, S.; Price, T. J.; Shepherd, L.; Au, H.-J.; Langer, C.; Moore, M. J.; Zalcberg, J. R. New England Journal of Medicine 2008, 359, 1757-1765.
28. Josephy, P. D.; Eling, T.; Mason, R. P. Journal of Biological Chemistry 1982, 257, 3669-75.
29. Gao, L. Z.; Zhuang, J.; Nie, L.; Zhang, J. B.; Zhang, Y.; Gu, N.; Wang, T. H.; Feng, J.; Yang, D. L.; Perrett, S.; Yan, X. Nat Nanotechnol 2007, 2, 577-583.
30. Gao, L. Z.; Wu, J. M.; Lyle, S.; Zehr, K.; Cao, L. L.; Gao, D. J Phys Chem C 2008, 112, 17357-17361.
31. Haberkorn, U.; Strauss, L. G.; Reisser, C.; Haag, D.; Dimitrakopoulou, A.; Ziegler, S.; Oberdorfer, F.; Rudat, V.; Vankaick, G. J. Nucl. Med. 1991, 32, 1548-1555.
32. Zeng, D.; Guo, Y.; White, A. G.; Cai, Z.; Modi, J.; Ferdani, R.; Anderson, C. J. Mol Pharmaceut 2014, 11, 3980-3987.
33. Zeng, D. X.; Ouyang, Q.; Cai, Z. X.; Xie, X. Q.; Anderson, C. J. Chem Commun 2014, 50, 43-45.

Various references are cited in this document, which are hereby incorporated by reference in their entireties herein.

What is claimed is:

1. A bioconjugate comprising:
   (a) a superparamagnetic iron oxide nanoparticle functionalized with a first bioorthogonal ligation moiety selected from the group consisting of tetrazine, an azide, a tetrazole, and combinations thereof, wherein the nanoparticle has a diameter of about 4 nm to about 8 nm; and
   (b) a glucose oxidase conjugated to the superparamagnetic iron oxide nanoparticle, wherein the glucose oxidase is functionalized with a second bioorthogonal ligation moiety selected from the group consisting of trans-cyclooctene, cyclooctyne, an alkyne, an alkene, photo-DIBO, cyclopropenone, and combinations thereof.

2. The bioconjugate of claim 1, further comprising a targeting probe, wherein the targeting probe is the antibody cetuximab, wherein the antibody cetuximab is conjugated to the glucose oxidase.

3. The bioconjugate of claim 2, further comprising a first spacer disposed between the iron oxide nanoparticle and the glucose oxidase.

4. The bioconjugate of claim 3, further comprising a second spacer disposed between the iron oxide nanoparticle and the targeting probe.

5. The bioconjugate of claim 3, further comprising a second spacer disposed between the glucose oxidase and the targeting probe.

6. The bioconjugate of claim 1, wherein the ratio between the iron oxide nanoparticle and the glucose oxidase is from about 1:100 to about 100:1.

7. A pharmaceutical composition comprising an effective amount of the bioconjugate of claim 1.

* * * * *